US011123363B2

(12) United States Patent
Klaerner et al.

(10) Patent No.: US 11,123,363 B2
(45) Date of Patent: Sep. 21, 2021

(54) POTASSIUM-BINDING AGENTS FOR TREATING HYPERTENSION AND HYPERKALEMIA

(71) Applicant: Vifor (International) Ltd., St. Gallen (CH)

(72) Inventors: Gerrit Klaerner, Los Gatos, CA (US); Lance Berman, San Francisco, CA (US)

(73) Assignee: VIFOR (INTERNATIONAL) LTD., St. Gallen (CH)

( * ) Notice: Subject to any disclaimer, the term of this patent is extended or adjusted under 35 U.S.C. 154(b) by 0 days.

(21) Appl. No.: 15/916,617

(22) Filed: Mar. 9, 2018

(65) Prior Publication Data
US 2018/0193377 A1 Jul. 12, 2018

Related U.S. Application Data

(63) Continuation of application No. 15/287,179, filed on Oct. 6, 2016, now Pat. No. 9,925,212, which is a (Continued)

(51) Int. Cl.
*A61K 9/00* (2006.01)
*A61K 31/78* (2006.01)
(Continued)

(52) U.S. Cl.
CPC ............... *A61K 31/78* (2013.01); *A61K 9/14* (2013.01); *A61K 31/7004* (2013.01);
(Continued)

(58) Field of Classification Search
CPC ..................................................... A61K 31/78
See application file for complete search history.

(56) References Cited

U.S. PATENT DOCUMENTS

| 2,340,111 A | 1/1944 | D'Alelio |
| 2,611,730 A | 9/1952 | Heming |

(Continued)

FOREIGN PATENT DOCUMENTS

| EP | 0349453 A1 | 1/1990 |
| EP | 0730494 A1 | 9/1996 |

(Continued)

OTHER PUBLICATIONS https://www.merriam-webster.com/dictionary/load#medicalDictionary, accessed Apr. 24, 2021.*

(Continued)

*Primary Examiner* — Paul W Dickinson
(74) *Attorney, Agent, or Firm* — Stinson LLP

(57) ABSTRACT

The present invention generally relates to methods of treating hypertension (HTN) in patients in need thereof wherein the patient optionally further suffers from chronic kidney disease (CKD) or Type II diabetes mellitus (T2DM). The invention also relates to methods of treating hyperkalemia in a patient in need thereof, wherein the patient suffers from CKD, T2DM or HTN and are optionally being treated with an effective amount of a renin-angiotensin-aldosterone system (RAAS) agent. The invention also relates to methods of treating kidney disease in a patient in need thereof, wherein the patient is optionally being treated with an effective amount of a renin-angiotensin-aldosterone system (RAAS) agent. The methods can comprise administering an effective amount of a potassium-binding agent to the patient to lower the patient's blood pressure and/or increase or stabilize the patient's kidney function.

33 Claims, 5 Drawing Sheets

Related U.S. Application Data continuation of application No. 14/581,698, filed on Dec. 23, 2014, now Pat. No. 9,492,476, which is a continuation of application No. PCT/US2013/063921, filed on Oct. 8, 2013.

(60) Provisional application No. 61/711,184, filed on Oct. 8, 2012.

(51) Int. Cl.

| | | |
|---|---|---|
| *A61K 31/7004* | (2006.01) | |
| *A61K 9/14* | (2006.01) | |
| *A61K 33/06* | (2006.01) | |
| *A61K 33/24* | (2019.01) | |
| *B01J 39/20* | (2006.01) | |

(52) U.S. Cl.
CPC .............. *A61K 33/06* (2013.01); *A61K 33/24* (2013.01); *B01J 39/20* (2013.01)

(56) References Cited

U.S. PATENT DOCUMENTS

| | | |
|---|---|---|
| 2,798,053 A | 7/1957 | Brown |
| 2,909,462 A | 10/1959 | Warfield et al. |
| 3,499,960 A | 3/1970 | Macek et al. |
| 3,874,907 A | 4/1975 | Gardon et al. |
| 3,974,272 A | 8/1976 | Polli et al. |
| 4,143,130 A | 3/1979 | Imondi et al. |
| 4,191,812 A | 3/1980 | Chong |
| 4,470,975 A | 9/1984 | Berger et al. |
| 4,492,205 A | 1/1985 | Jundt et al. |
| 4,605,701 A | 8/1986 | Harada et al. |
| 4,747,881 A | 5/1988 | Shaw et al. |
| 4,837,015 A | 6/1989 | Olsen |
| 4,902,501 A | 2/1990 | Bandi et al. |
| 4,942,205 A | 7/1990 | Ohmori et al. |
| 5,051,253 A | 9/1991 | Lloyd-Jones et al. |
| 5,091,175 A | 2/1992 | Imondi et al. |
| 5,141,927 A | 8/1992 | Krotkiewski |
| 5,186,937 A | 2/1993 | Sparks et al. |
| 5,188,825 A | 2/1993 | Iles et al. |
| 5,210,079 A | 5/1993 | Carini et al. |
| 5,238,924 A | 8/1993 | Smith |
| 5,281,631 A | 1/1994 | Horwitz et al. |
| 5,374,422 A | 12/1994 | St. Pierre et al. |
| 5,413,782 A | 5/1995 | Warchol et al. |
| 5,487,888 A | 1/1996 | Mandeville, III et al. |
| 5,607,669 A | 3/1997 | Mandeville, III et al. |
| 5,618,530 A | 4/1997 | Mandeville, III et al. |
| 5,633,344 A | 5/1997 | Figuly |
| 5,667,775 A | 9/1997 | Holmes-Farley et al. |
| 5,679,717 A | 10/1997 | Mandeville, III et al. |
| 5,693,675 A | 12/1997 | Mandeville, III et al. |
| 5,702,696 A | 12/1997 | Mandeville, III et al. |
| 5,718,920 A | 2/1998 | Notenbomer |
| 5,846,990 A | 12/1998 | Murugesan et al. |
| 5,935,599 A | 8/1999 | Dadey |
| 6,280,717 B1 | 8/2001 | Kamakura et al. |
| 6,294,163 B1 | 9/2001 | Dhal et al. |
| 6,383,500 B1 | 5/2002 | Wooley et al. |
| 6,498,142 B1 | 12/2002 | Sampath et al. |
| 6,747,020 B2 | 6/2004 | Perez et al. |
| 6,881,484 B2 | 4/2005 | Kataoka et al. |
| 7,556,799 B2 | 7/2009 | Charmot et al. |
| 8,147,873 B2 | 4/2012 | Charmot et al. |
| 8,216,560 B2 | 7/2012 | Charmot et al. |
| 8,282,913 B2 | 10/2012 | Charmot et al. |
| 8,287,847 B2 | 10/2012 | Charmot et al. |
| 8,337,824 B2 | 12/2012 | Albrecht et al. |
| 8,475,780 B2 | 7/2013 | Charmot et al. |
| 8,778,324 B2 | 7/2014 | Charmot et al. |
| 8,889,115 B2 | 11/2014 | Charmot et al. |
| 2002/0054903 A1 | 5/2002 | Tyler et al. |
| 2002/0054913 A1 | 5/2002 | Heese et al. |
| 2002/0146386 A1 | 10/2002 | Simon et al. |
| 2003/0027789 A1 | 2/2003 | Yamaoka et al. |
| 2003/0065090 A1 | 4/2003 | Kelly et al. |
| 2004/0105895 A1* | 6/2004 | Ash ............... A61K 33/00 424/617 |
| 2004/0166156 A1 | 8/2004 | Tyler et al. |
| 2004/0251204 A1 | 12/2004 | Paananen et al. |
| 2005/0036983 A1 | 2/2005 | Simon et al. |
| 2005/0220751 A1 | 10/2005 | Charmot et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2006/0024336 A1 | 2/2006 | Charmot et al. |
| 2007/0092553 A1 | 4/2007 | Tengler et al. |
| 2007/0248564 A1 | 10/2007 | Wilson et al. |
| 2009/0155370 A1* | 6/2009 | Cope ............... A61K 9/5026 424/497 |
| 2010/0104527 A1 | 4/2010 | Mansky et al. |
| 2010/0111892 A1 | 5/2010 | Chang et al. |
| 2011/0123604 A1 | 5/2011 | Strickland et al. |
| 2011/0236340 A1 | 9/2011 | Mansky et al. |
| 2012/0077690 A1* | 3/2012 | Singbartl ............ G01N 33/6893 506/9 |
| 2012/0107381 A1* | 5/2012 | Reddy ................. A61K 9/0095 424/405 |
| 2012/0141581 A1* | 6/2012 | Withington .......... A61K 9/4858 424/452 |
| 2012/0213847 A1* | 8/2012 | Keyser ................. A61K 9/143 424/451 |
| 2013/0131202 A1 | 5/2013 | Albrecht et al. |
| 2013/0189216 A1 | 7/2013 | Albrecht et al. |
| 2013/0197170 A1 | 8/2013 | Tyson |
| 2013/0272990 A1 | 10/2013 | Charmot et al. |
| 2014/0105848 A1 | 4/2014 | Klaerner et al. |
| 2014/0171595 A1 | 6/2014 | Connor et al. |
| 2014/0221681 A1 | 8/2014 | Mu |
| 2014/0286891 A1 | 9/2014 | Charmot et al. |

FOREIGN PATENT DOCUMENTS

| | | |
|---|---|---|
| JP | 1998-059851 A | 3/1998 |
| JP | 1998-130154 A | 5/1998 |
| JP | 2004-149525 A | 5/2004 |
| WO | 82/00257 A1 | 2/1982 |
| WO | 92/10522 A1 | 6/1992 |
| WO | 94/27619 A1 | 12/1994 |
| WO | 95/14531 A1 | 6/1995 |
| WO | 97/49387 A1 | 12/1997 |
| WO | 97/49736 A2 | 12/1997 |
| WO | 00/40224 A1 | 7/2000 |
| WO | 01/51063 A1 | 7/2001 |
| WO | 02/12160 A1 | 2/2002 |
| WO | 02/40039 A2 | 5/2002 |
| WO | 02/062356 A2 | 8/2002 |
| WO | 2005/065291 A2 | 7/2005 |
| WO | 2005/094384 A2 | 10/2005 |
| WO | 2007/038801 A2 | 4/2007 |
| WO | 2007/038802 A2 | 4/2007 |
| WO | 2009/029829 A1 | 3/2009 |
| WO | 2010/022382 A2 | 2/2010 |
| WO | 2010/022383 A2 | 2/2010 |
| WO | 2010/132662 A1 | 11/2010 |
| WO | 2012/097017 A1 | 7/2012 |
| WO | 2014/015240 A1 | 1/2014 |

OTHER PUBLICATIONS

Shen, High drug-loading nanomedicines: progress, current status, and prospects, Int. J. Nanomedicine, 2017, 12, 4085-4109.*

Agarwal, et al., "Pathophysiology of Potassium Absorption and Secretion by the Human Intestine", Gastroenterology, 1994, pp. 548-571, vol. 107, American Gastroenterological Association.

Atkins, R. C., et al., "Proteinuria Reduction and Progression to Renal Failure in Patients with Type 2 Diabetes Mellitus and Overt Nephropathy," American Journal of Kidney Diseases, Feb. 2005, pp. 281-287, vol. 45, No. 2.

(56) References Cited

OTHER PUBLICATIONS

Berlyne, G. M., et al., "Cation Exchange Resins in Hyperkalaemic Renal Failure", Israel J. Med Sci., 1967, pp. 45-52, vol. 3, No. 1.

Blake, J., M.D., et al., "Differential Effects of Direct Antagonism of AII Compared to ACE Inhibitors on Serum Potassium Levels and Azotemia in Patients with Severe Congestive Heart Failure," Congestive Heart Failure, Jul./Aug. 2000, pp. 193-196, vol. 6, No. 4, CHF, Inc., Darien, Connecticut.

Brenerman, M. L., et al., "Interaction of Polyacids with Alkali-Halide Metals and of Tetramethyl Ammonium in Alcohols and Alcohol-Water Mixtures," Chemistry and Chemical Technology, 1986, pp. 56-60, vol. 8, No. 29.

Brenner, B. M., et al., "Effects of Losartan on Renal and Cardiovascular Outcomes in Patients with Type 2 Diabetes and Nephropathy," The New England Journal of Medicine, Sep. 20, 2001, pp. 861-869, vol. 345, No. 12.

Bussemaker, E., et al., "Pathogenesis of Hypertension: Interactions Among Sodium, Potassium, and Aldosterone," American Journal of Kidney Diseases, Jun. 2010, pp. 1111-1120, vol. 55, No. 6.

Buysse, J. M., et al., "Pearl-HF: Prevention of Hyperkalemia in Patients with Heart Failure Using a Novel Polymeric Potassium Binder, RLY5016," Future Cardiology, Jan. 2012, pp. 17-28, vol. 8, No. 1.

Chernin, G., et al., "Secondary Prevention of Hyperkalemia With Sodium Polystyrene Sulfonate in Cardiac and Kidney Patients on Renin-Angiotensin-Aldosterone System Inhibition Therapy," Clinical Cardiology, 2012, pp. 32-36, vol. 35, No. 1.

Chourasia, M. K., et al., "Pharmaceutical Approaches to Colon Targeted Drug Delivery Systems", J. Pharm Pharm Sci., 2003, pp. 33-66, vol. 6, No. 1.

Coli, L., et al., "Phosphate Removal by Resin Hemoperfusion Efficacy and Biocompatibility of a New Exchange Resin", Biomaterials, Artificial Cells, and Immobilization Biotechnology, 1992, pp. 1153-1163, vol. 20, No. 5.

Corcoran, A. C., et al., "Controlled Observations on the Effect of Low Sodium Dietotherapy in Essential Hypertension", Circulation, 1951, pp. 1-16, vol. 3, No. 1.

Cuna, M. et al., "Controlled-Release Liquid Suspensions Based on Ion-Exchange Particles Entrapped Within Acrylic Microcapusles", International Journal of Pharmaceutics, 2000, pp. 151-158, vol. 199, Elsevier Science.

Dai, et al., "Controlling Ion Transport through Mulitlayer Polyelectrolyte Membranes by Derivatization with Photolabile Functional Groups", Macromolecules, 2002, pp. 3164-3170, vol. 35, American Chemical Society.

Danowski, T. S., et al., "Changes in Fecal and Serum Constituents During Ingestion of Cation and Anion Exchangers", Ann N Y Acad. Sci., 1953, pp. 273-279, vol. 57, No. 3.

Emerson Jr., K., et al., "The Role of the Gastro-Intestinal Tract in the Adaptation of the Body to the Prevention of Sodium Depletion by Cation Exchange Resins", Ann N Y Acad Sci., 1953, pp. 280-290, vol. 57, No. 3.

Emmett, M., et al., "Effect of Three Laxatives and a Cation Exchange Resin on Fecal Sodium and Potassium Excretion", Gastroenterology, 1995, pp. 752-760, vol. 108, No. 3.

Estrela-Lopis, et al., "Sans Studies of Polyelectrolyte Multilayers on Colloidal Templates", Langmuir, 2002, pp. 7861-7866, vol. 18, American Chemical Society.

Evans, B. M., et al., "Ion-Exchange Resins in the Treatment of Anuria", Lancet, 1953, pp. 791-795, vol. 265, Number 6790.

Field, Jr., H., et al., "Electrolyte Changes in Ileal Contents and in Feces During Restriction of Dietary Sodium With and Without the Administration of Cation-Exchange Resin", Circulation, 1955, pp. 625-629, vol. 12, No. 4.

Field, Jr., H., et al., "Mechanisms Regulating the Retention of Sodium in the Feces by Cation-Exchange Resin: Release of Base from the Resin by Bacterial Fermentation in the Terminal Ileum", J. Lab Clin Med., 1958, pp. 178-184, vol. 51, No. 2.

Forrest, M. L., et al., "A Degradable Polyethylenimine Derivative with Low Toxicity for Highly Efficient Gene Delivery", Bioconjugate Chem., 2003, pp. 934-940, vol. 14, No. 5.

Fourman, P., "Capacity of a Cationic Exchange Resin (zeo-karb 225) in Vivo" British Medical Journal, 1953, pp. 544-546, vol. 1, No. 4809.

Friedman, E. A., "Clinical Aspects of Uremia and Dialysis/Sorbent Therapy in Uremia", 1976, pp. 671-687.

Friedman, E. A., et al., "Combined Oxystarch-Charcoal Trial in Uremia: Sorbent-induced Reduction in Serum Cholesterol", Kidney International, 1976, pp. S273-S276, vol. 10.

Gerstman, et al., "Use of Sodium Polystyrene Sulfonate in Sorbitol in the United States", American Journal of Kidney Diseases, Nov. 1991, pp. 619-621, vol. XVIII, No. 5.

Greenman, L., et al., "Biochemical Changes Accompanying the Ingestion of a Carboxylic Cation Exchanger in the Hydrogen, Ammonium, Sodium, Potassium, or Calcium Form", J. Clin Invest., 1951, pp. 995-1008, vol. 30, No. 9.

Gruy-Kapral, C., et al., "Effect of Single Dose Resin-Cathartic Therapy on Serum Potassium Concentration in Patients With End-Stage Renal Disease", J. Am. Soc. Nephrol, 1998, pp. 1924-1930, vol. 9, No. 10.

Harthon, J. G. L., et al., "A Case of Uremia and Hyperpotassemia Treated With Sulphonic Cation-Exchange Resin", Acta Med. Scan, 1952, pp. 230-236, vol. 144, No. 3.

He, F. J., et al., "Effect of Short-Term Supplementation of Potassium Chloride and Potassium Citrate on Blood Pressure in Hypertensives," Hypertension, Journal of the American Heart Association, 2005, pp. 571-574, vol. 45.

Heming, A. E., et al., "Considerations in the Selection of Cation Exchange Resins for Therapeutic Use", Ann N Y Acad Sci., 1953, pp. 239-251, vol. 57, No. 3.

Himathongkam, T., et al., "Potassium-Aldosterone-Renin Interrelationships," The Journal of Clinical Endocrinology and Metabolism, 1975, pp. 153-159, vol. 41, No. 1.

Houston, M. C., "The Importance of Potassium in Managing Hypertension," Current Hypertension Reports, Aug. 2011, pp. 309-317, vol. 13, No. 4.

Ichikawa, H. et al., "Use of Ion-Exchange Resins to Prepare 100 μm-sized Microcapsules with Prolonged Drug-Release by the Wurster Process", International Journal of Pharmaceutics, 2001, pp. 67-76, vol. 216, Elsevier Science.

Imondi, A. R., et al., "Gastrointestinal Sorbents for the Treatment of Uremia I. Lightly Cross-Linked Carboxyvinyl Polymers", Ann Nutr Metabol., 1981, pp. 311-319, vol. 25, No. 5.

International Search Report and Written Opinion issued for PCT/US2013/063921, dated Sep. 1, 2014, 21 pages.

Invitation to Pay Additional Fees and, Where Applicable, Protest Fee issued for PCT/US2013/063921, dated Jun. 4, 2014, 6 pages.

Irwin, L., et al., "The Effect of a Cation Exchange Resin on Electrolyte Balance and Its Use in Edematous States", J. Clin Invest., 1949, pp. 1403-1411, vol. 28, No. 6, Part 2.

Johnson, K., et al., "Sodium Polystyrene Sulfonate Resin Candy for Control of Potassium in Chronic Dialysis Patients," Clinical Nephrology, 1976, pp. 266-268, vol. 5, No. 6.

Kim, et al., "Therapeutic Approach to Hyperkalemia", Nephron, 2002, pp. 33-40, vol. 92, Supplement 1, Division of Nephrology, Department of Internal Medicine, Hanyang University Kuri Hospital, Kuri, Korea.

Kohlstaedt, K. G., et al., "Clinical Experience With Mixtures of Anion and Cation Exchange Resins", Ann N Y Acad Sci., 1953, pp. 260-272, vol. 57, No. 3.

Koping-Hoggard, M., et al., "Chitosan as a Nonviral Gene Delivery System. Structure-Property Relationships and Characteristics Compared with Polyethylenimine in Vitro and After Lung Administration in Vivo", Gene Therapy, 2001, pp. 1108-1121, vol. 8.

Lewis, E. J., et al., "Renoprotective Effect of the Angiotensin-Receptor Antagonist Irbesartan in Patients with Nephropathy Due to Type 2 Diabetes," The New England Journal of Medicine, Sep. 20, 2001, pp. 851-860, vol. 345, No. 12.

Mason, N. S., et al., "A New Ion Exchanger With High in Vivo Sodium Capacity" Kidney Int. Suppl., 1985, pp. S178-S182, vol. 28, No. 17.

(56) References Cited

OTHER PUBLICATIONS

Mateer, F. M., et al., "Sodium Restriction and Cation Exchange Resin Therapy in Nephrotic Children", J Clin Invest, 1951, pp. 1018-1026, vol. 30, No. 9.
McChesney, E.W., "Effects of Long-Term Feeding of Sulfonic Ion Exchange Resin on the Growth and Mineral Metabolism of Rats", Am. J. Physiol., 1954, pp. 395-400, vol. 177, No. 3.
McChesney, E. W., et al., "Some Aspects of Cation Exchange Resins as Therapeutic Agents for Sodium Removal", Ann N Y Acad Sci., 1953, pp. 252-259, vol. 57, No. 3.
Meszaros, et al., "Adsorption of Poly(ethyleneimine) on Silica Surfaces: Effect of pH on the Reversibility of Adsorption", Langmuir, 2004, pp. 5026-5029, vol. 20, American Chemical Society.
Miao, Y., et al., "Increased Serum Potassium Affects Renal Outcomes: A Post Hoc Analysis of the Reduction of Endpoints in NIDDM with the Angiotensin II Antagonist Losartan (RENAAL) Trial," Diabetologia, 2010, pp. 44-50, vol. 54, No. 1.
Morris, Jr., R. C., et al., "Normotensive Salt Sensitivity: Effects of Race and Dietary Potassium," Hypertension, Journal of the American Heart Association, 1999, pp. 18-23, vol. 33.
Morris, Jr., R. C., et al., "Relationship and Interaction Between Sodium and Potassium," Journal of the American College of Nutrition, 2006, pp. 262S-270S, vol. 25, No. 3.
Moustafine, R. I., et al., "Characteristics of Interpolyelectrolyte Complexes of Eudragit E 100 With Sodium Alginate", Int. J. Pharm., 2005, pp. 113-120, vol. 294, Nos. 1-2.
Palmer, B. F., "Managing Hyperkalemia Caused by Inhibitors of the Renin-Angiotensin-Aldosterone System," The New England Journal of Medicine, Aug. 5, 2004, pp. 585-592, vol. 351, No. 6.
Picart, et al., "Microinterferometric Study of the Structure, Interfacial Potential, and Viscoelastic Properties of Polyelectrolyte Multilayer Films on a Planar Substrate", J. Phys. Chem. B, 2004, pp. 7196-7205, vol. 108, American Chemical Society.
Pitt, B., "Effect of Aldosterone Blockade in Patients with Systolic Left Ventricular Dysfunction: Implications of the Rales and Ephesus Studies," Molecular and Cellular Endocrinology, 2004, pp. 53-58, vol. 217.
Pitt, B., et al., "The Effect of Spironolactone on Morbidity and Mortality in Patients with Severe Heart Failure," The New England Journal of Medicine, Sep. 2, 1999, pp. 709-717, vol. 341, No. 10.
Pitt, B., et al., "A Multicenter, Open-Label, Single-Arm Study to Evaluate a Titration Regimen for the Potassium Binding Polymer RLY5016 in Patients with Heart Failure and Chronic Kidney Disease (RLY5016-204)," Poster Presentation, Presented at the European Society of Cardiology Congress 2011 in Paris, France on Aug. 30, 2011, 1 page.
Root, M. A., "Comparison of the in Vivo Sodium-Removing Activity of Various Types of Ion Exchange Resins in Rats", J. Lab. Clin. Med., 1953, pp. 430-437, vol. 42, No. 3.
Ross, E. J. et al., "Observations on Cation Exchange Resins in the Small and Large Intestines", 1954, pp. 555-566, Medical Unit, University College Hospital Medical School, London, W.C.1.
Salas-Coll, et al., "Potassium Transport Across the Distal Colon in Man", Clinical Science and Molecular Medicine, 1976, pp. 287-296, vol. 51.
Scherr, L., et al., "Management of Hyperkalemia with a Cation-Exchange Resin," The New England Journal of Medicine, Jan. 19, 1961, pp. 115-119, vol. 264, No. 3.
Spencer, et al., "Cation Exchange in the Gastrointestinal Tract", 1954, pp. 603-606, Medical Unit, University College Hospital Medical School, London, W.C.1.
Thies, C., "Microcapsules as Drug Delivery Devices," Crit Rev Biomed Eng., 1982, pp. 335-383, vol. 8, No. 4.
Thomas, M., et al., "Cross-Linked Small Polyethylenimines: While Still Nontoxic, Deliver DNA Efficiently to Mammalian Cells in Vitro and in Vivo", Pharmaceutical Research, 2005, pp. 373-380, vol. 22, No. 3.
Tust, R. H., et al., "The Effects of Malethamer on the Excretion and Plasma Levels of Sodium, Potassium, and Chloride (34990)", Proc. Soc. Exp. Biol. Med., 1970, pp. 72-76, vol. 135, No. 1.

Williams, G. H., et al., "Studies of the Control of Plasma Aldosterone Concentration in Normal Man," The Journal of Clinical Investigation, Jul. 1972, pp. 1731-1742, vol. 51.
Williams, G. H., et al., "Studies of the Control of Plasma Aldosterone Concentration in Normal Man," The Journal of Clinical Investigation, Oct. 1972, pp. 2645-2652, vol. 51.
Wrong, O., et al., "The Electrolyte Content Faeces", Proc. R. Soc. Med., 1965, pp. 1007-1009, vol. 58, No. 12.
Wrong, O.M., "The Role of the Human Colon in Homeostasis", Scientific Basis of Medicine Annual Reviews, 1971, pp. 192-215.
Wrong, et al., "In Vivo Dialysis of Feces as a Method of Stool Analysis", Clinical Science, 1965, pp. 357-375, vol. 28.
Zannad, F., et al., "Rationale and Design of the Eplerenone in Mild Patients Hospitalization and Survival Study in Heart Failure (Emphasis-HF)," European Journal of Heart Failure, 2010, pp. 617-622, vol. 12, No. 6.
Zeeuw, D. D., et al., "Proteinuria, A Target for Renoprotection in Patients with Type 2 Diabetic Nephropathy: Lessons from RENAAL," Kidney International, 2004, pp. 2309-2320, vol. 65.
Gennari, F. J., et al., "Hyperkalemia: An Adaptive Response in Chronic Renal Insufficiency," Kidney International, Jul. 2002, pp. 1-9, vol. 62, No. 1.
Pitt, B., et al., "Evaluation of the Efficacy and Safety of RLY5016, A Polymeric Potassium Binder, in a Double-Blind, Placebo-Controlled Study in Patients with Chronic Heart Failure (the Pearl-HF) Trial," European Heart Journal, 2011, pp. 820-828, vol. 32, No. 7.
Van Der Meer, P., et al., "To Bind or Not to Bind: Potassium-Lowering Drugs in Heart Failure," European Heart Journal, 2011, pp. 791-792, vol. 32, No. 7.
Ellis, F. W., et al., "Sugar Alcohols XXII. Metabolism and Toxicity Studies with Mannitol and Sorbitol in Man and Animals," Journal of Biological Chemistry, 1941, pp. 147-154, vol. 141.
Gruy-Kapral, C., et al., "Effect of Single Dose Resin-Cathartic Therapy on Serum Potassium Concentration in Patients with End-Stage Renal Disease," Journal of the American Society of Nephrology, Oct. 1998, pp. 1924-1930, vol. 9, No. 10.
Gumz, M. L., et al., "Role of Circadian Rhythms in Potassium Homeostasis," Seminars in Nephrology, May 2013, pp. 229-236, vol. 33, No. 3.
"Mannitol and Sorbitol," Federal Register, Jul. 26, 1973, pp. 20046-20048, vol. 38, No. 143.
Mcgowan, C. E., et al., "Intestinal Necrosis Due to Sodium Polystyrene Sulfonate (Kayexalate) in Sorbitol," Southern Medical Journal, May 2009, pp. 493-497, vol. 102, No. 5.
Sterns, R. H., et al., "Ion-Exchange Resins for the Treatment of Hyperkalemia: Are They Safe and Effective?," Journal of the American Society of Nephrology, 2010, pp. 733-735, vol. 21, No. 5.
Weir, M. R., et al., "Patiromer in Patients with Kidney Disease and Hyperkalemia Receiving RAAS Inhibitors," The New England Journal of Medicine, Jan. 15, 2015, pp. 211-221, vol. 372, No. 3 (including Supplementary Appendix).
Nishizaka, Mari K. et al., Use of Aldosterone Antagonists in Resistant Hypertension, www.medscape.com/viewarticle/487958_print. Retrieved on Apr. 6, 2017, 3 pages.
Bronzino, Joseph D., The Biomedical Engineering Handbook (Second Edition), vol. II, 2000, Chapter 105—Vaccine Production, 18 pages.
Einhorn, Lisa M. et al., The Frequency of Hyperkalemia and Its Significance in Chronic Kidney Disease, Archives nternal Med, vol. 169, No. 12, Jun. 22, 2009, pp. 1156-1162.
Fluids & Electrolytes: A 2-in-1 Reference for Nurses, Chapter 6—Potassium imbalances, 2005, pp. 85-101.
Handbook of Pharmaceutical Excipients, Fifth Edition, 2006, pp. 449-453 and pp. 718-721.
Hsieh, Ming-Fang et al., Higher Serum Potassium Level Associated with Late Stage Chronic Kidney Disease, Chang Gung Med J vol. 34, No. 4 (2011), pp. 418-425.
Excipient Development for Pharmaceutical, Biotechnology, and Drug Delivery Systems, Chapter 17—Excipients for Protein Drugs (2006), pp. 291-332.

(56) References Cited

OTHER PUBLICATIONS

Kionex Prescribing Information, Paddock Laboratories, LLC, Nov. 2018, 7 pages.
Makarovsky, Igor et al., Toxic Chemical Compounds, Hydrogen Fluoride—The Protoplasmic Poison, Israel Medical Association Journal, vol. 10 (2008), pp. 381-385.
Relypsa News Release, May 23, 2011, Relypsa Announces Presentation of Positive Phase 2 Results for RLY5016 at American Society of Hypertension Meeing, 1 page.
Sood, Manish M. et al., Emergency Management and Commonly Encountered Outpatient Scenarios in Patients With Hyperkalemia, Mayo Clinic Proc. 2007; 82(12); pp. 1553-1561.
Tomino, Y. et al., Dose-response to a jelly preparation of calcium polystyrene sulfonate in patients with hyperkalemia—changes in serum potassium levels with or without a RAAS inhibitor, Clinical Nephrology, vol. 68, No. 6 (2007), pp. 379-385.
Pharmacotherapeutics for Advanced Practice, Second Edition, Chapter 30—Constipation, Diarrhea and Irritable Bowel Syndrome (by Wilbur and Briscoe), 2006, pp. 386-414.
Arakawa, Tsutomu et al., Stabilization of Protein Structure by Sugars, Biochemistry (1982) vol. 21, pp. 3536-6544.
Ma, T.S., Determination of Fluorine in Quantitative Organic Microanalysis, Analytical Chem, 1958, vol. 30, No. 9, pp. 1557-1560.
Fessenden, Ralph J. et al., Organic Chemistry (4th Edition)(1990), Chapter 14 Carboxylic Acids, pp. 591-617.

* cited by examiner

POTASSIUM-BINDING AGENTS FOR TREATING HYPERTENSION AND HYPERKALEMIA

CROSS-REFERENCE TO RELATED APPLICATIONS

This application is a continuation of U.S. patent application Ser. No. 15/287,179 filed Oct. 6, 2016, which is a continuation of U.S. patent application Ser. No. 14/581,698 filed Dec. 23, 2014 (issued as U.S. Pat. No. 9,492,476) which is a continuation of PCT Patent Application No. PCT/US2013/063921, filed on Oct. 8, 2013 which claims the benefit of U.S. Provisional Patent Application Ser. No. 61/711,184, filed on Oct. 8, 2012. The entire content of the above applications are hereby incorporated by reference.

FIELD OF THE INVENTION

The present invention generally relates to methods of treating hypertension (HTN) in patients in need thereof wherein the patient optionally further suffers from chronic kidney disease (CKD) or Type II diabetes mellitus (T2DM). The invention also relates to methods of treating kidney disease in a patient in need thereof, wherein the patient is optionally being treated with an effective amount of a renin-angiotensin-aldosterone system (RAAS) agent. The invention also relates to methods of treating hyperkalemia in a patient in need thereof, wherein the patient suffers from CKD, T2DM or HTN and are optionally being treated with an effective amount of a renin-angiotensin-aldosterone system (RAAS) agent. The methods can comprise administering an effective amount of a potassium-binding agent to the patient to lower the patient's blood pressure and/or increase or stabilize the patient's kidney function.

BACKGROUND OF THE INVENTION

Normal kidney function is critical for the maintenance of potassium homeostasis. The ability of the kidney to maintain potassium homeostasis depends on several factors, including the normal production of aldosterone, sodium delivery to the distal nephron, and adequate sodium-potassium exchange in the cortical collecting duct (Palmer, B. F., N. Engl. J. Med. 2004, 351:585-92). Of these factors, aldosterone production and action is closely regulated by the renin-angiotensin-aldosterone system (RAAS), a cornerstone of the regulatory components controlling blood pressure, blood volume and cardiovascular function. RAAS inhibition, designed to limit aldosterone production and function, is therefore an important treatment strategy for hypertension, diabetes, chronic kidney disease and heart failure. Several studies have demonstrated the renal protective effects of angiotensin receptor blockers (ARBs) such as losartan or irbesartan (Brenner, B. M. et al., N. Engl. J. Med. 2001, 345:861-869; de Zeeuw, D. et al. Kidney Intl. 2004, 65:2309-2320; Miao, Y. et al., Diabetologia 2010; Lewis, E. J. et al., N. Engl. J. Med. 2001, 345:851-860; Atkins, R. C. et al., Am. J. Kidney Dis. 2005, 45:281-287), while studies using dual blockade of the RAAS with an aldosterone antagonist (spironolactone or eplerenone), added to either angiotensin converting enzyme inhibitor (ACEI) or ARB therapy, were shown to substantially reduce cardiovascular endpoints in heart failure or post-myocardial infarction patients (Pitt, B. et al., N. Engl. J. Med. 1999, 341:709-717; Pitt, B., Molecular & Cellular Endocrinol. 2004, 217:53-58; Zannad, F. et al., European J. Heart Failure 2010).

Despite the demonstrated clinical benefits of RAAS inhibitors, the fundamental mode of action of the drugs disturbs the exchange of sodium for potassium in the kidney tubule. As a result, potassium retention can precipitate hyperkalemia, defined as a serum potassium value >5.0 mEq/L. This is particularly problematic in patients with reduced renal function resulting from chronic kidney disease and common co-morbidities such as hypertension, diabetes and heart failure. In this situation, the combination of RAAS inhibition and reduced renal function can aggravate the nascent positive potassium balance and trigger a hyperkalemic event. The discontinuation or reduction in the dose of RAAS inhibitors is a common intervention for patients taking RAAS inhibitors who show abnormally elevated serum potassium levels, which deprives patients of the benefits of RAAS inhibitors. Thus, there is a need to control blood pressure in patients and treat hyperkalemia.

SUMMARY OF THE INVENTION

One aspect of the invention is a method of treating hypertension in a patient in need thereof. The method comprises administering an effective amount of a medication that controls the serum potassium of a patient in need thereof into the normal range. The method comprises administering an effective amount of a medication that controls the serum potassium of a patient in need thereof into the normal range within two days of treatment, and in particular with chronic dosing, and further with such chronic over a period of at least one month, more specifically at least 3 months, preferably at least 6 months and more preferably at least 9 months. More specifically, the method comprises administering an effective amount of a potassium binding agent, such as 2-fluoroacrylate-divinylbenzene-1,7-octadiene copolymer crosslinked in the salt or acid form, to the patient.

Another aspect is a method of treating hypertension in a chronic kidney disease patient in need thereof. The patient is optionally treated with an effective amount of a renin-angiotensin-aldosterone system (RAAS) agent and the method comprising administering an effective amount of a potassium binding agent, such as 2-fluoroacrylate-divinylbenzene-1,7-octadiene copolymer crosslinked in the salt or acid form, to the patient to control the patient's serum potassium into the normal range.

A further aspect is a method of treating hypertension in a heart failure patient in need thereof. The patient is optionally treated with an effective amount of a renin-angiotensin-aldosterone system (RAAS) agent and the method comprises administering an effective amount of a potassium binding agent, such as 2-fluoroacrylate-divinylbenzene-1,7-octadiene copolymer crosslinked in the salt or acid form, to the patient to control the patient's serum potassium into the normal range.

Yet another aspect is a method of treating hypertension in a type 2 diabetes mellitus patient in need thereof. The patient is optionally treated with an effective amount of a renin-angiotensin-aldosterone system (RAAS) agent and the method comprises administering an effective amount of a potassium binding agent, such as 2-fluoroacrylate-divinylbenzene-1,7-octadiene copolymer crosslinked in the salt or acid form, to the patient to control the patient's serum potassium into the normal range.

Yet a further aspect is a method of treating hyperkalemia in a chronic kidney disease patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by decreasing the patient's serum creatinine level as compared to the patient's serum creatinine level before treatment with 2-fluoroacrylate-divinylbenzene-1,7-octadiene copolymer crosslinked in the salt or acid form.

Another aspect of the invention is a method of treating hyperkalemia in a chronic kidney disease patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by increasing the time to progression of end stage renal disease as compared to a chronic kidney disease patient optionally treated with a RAAS agent but not treated with 2-fluoroacrylate-divinylbenzene-1,7-octadiene copolymer crosslinked in the salt or acid form.

A further aspect is a method of treating hyperkalemia in a chronic kidney disease patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by increasing survival as compared to a chronic kidney disease patient optionally treated with a RAAS agent but not treated with 2-fluoroacrylate-divinylbenzene-1,7-octadiene copolymer crosslinked in the salt or acid form.

Yet another aspect is a method of treating hyperkalemia in a chronic kidney disease patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by increasing or stabilizing estimated glomerular filtration rate (eGFR) as compared to the patient's eGFR before treatment with 2-fluoroacrylate-divinylbenzene-1,7-octadiene copolymer crosslinked in the salt or acid form.

Another aspect is a method of treating chronic kidney disease in a patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by decreasing the patient's serum creatinine level as compared to the patient's serum creatinine level before treatment with 2-fluoroacrylate-divinylbenzene-1,7-octadiene copolymer crosslinked in the salt or acid form.

A further aspect is a method of treating chronic kidney disease in a patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by increasing the time to progression of end stage renal disease as compared to a chronic kidney disease patient optionally treated with a RAAS agent but not treated with 2-fluoroacrylate-divinylbenzene-1,7-octadiene copolymer crosslinked in the salt or acid form.

Yet another aspect is a method of treating chronic kidney disease in a patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by increasing survival as compared to a chronic kidney disease patient optionally treated with a RAAS agent but not treated with 2-fluoroacrylate-divinylbenzene-1,7-octadiene copolymer crosslinked in the salt or acid form.

Another aspect is a method of treating chronic kidney disease in a patient in need thereof optionally being treated with an effective amount of a renin-angiotensin-aldosterone system (RAAS) agent. The method comprises administering an effective amount of 2-fluoroacrylate-divinylbenzene-1,7-octadiene copolymer crosslinked in the salt or acid form to the patient to increase or stabilize the patient's kidney function by increasing or stabilizing estimated glomerular filtration rate (eGFR) as compared to the patient's eGFR before treatment with 2-fluoroacrylate-divinylbenzene-1,7-octadiene copolymer crosslinked in the salt or acid form.

Other objects and features will be in part apparent and in part pointed out hereinafter.

DESCRIPTION OF THE PREFERRED EMBODIMENTS

Figure 1:
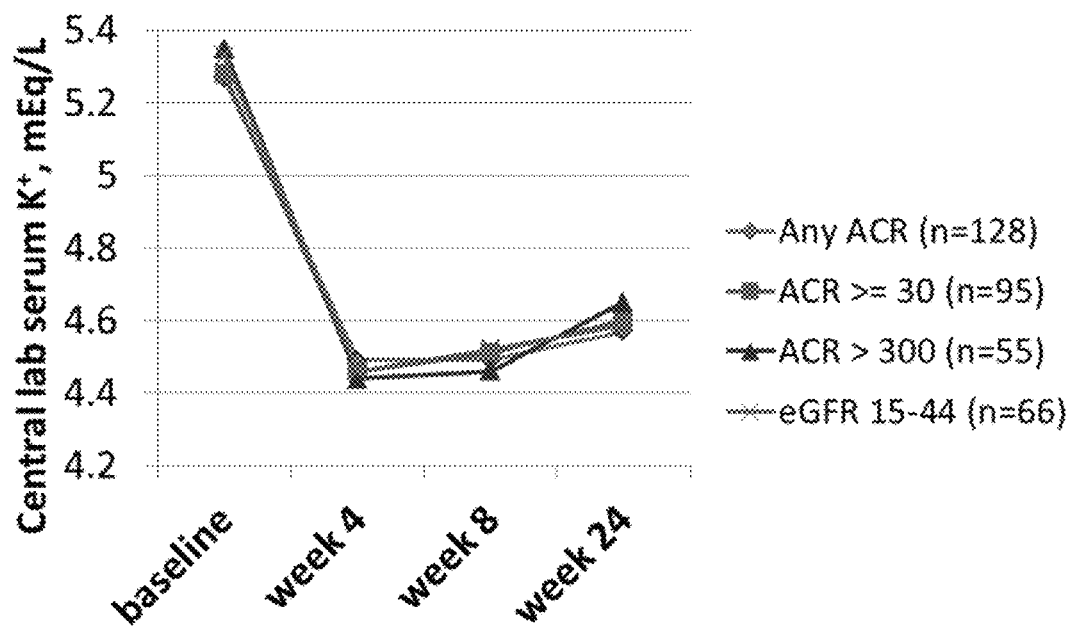
FIG. 1 is a graph of the central lab serum potassium concentration in mEq/L versus time of treatment for patients having been treated for six months with the protocol described in Example 2 and having any albumin creatinine ratio (ACR), an ACR≥30, and ACR>300 and an estimated glomerular filtration rate (eGFR) of 15-44 mL/min/1.73 $m^2$.

Hyperkalemia, which can present chronically or acutely, can lead to severe medical complications, including life-threatening cardiac arrhythmias and sudden death. Hyperkalemia is typically defined as a serum potassium level, or potassium in the blood, greater than 5.0 milliequivalents per liter (mEq/L). Patients with serum potassium levels greater than or equal to 5.5 mEq/L, which we define as moderate-to-severe hyperkalemia, were found in an independent study to have a 10-fold increase in their mortality rate within 24 hours. Hyperkalemia occurs most frequently in patients with chronic kidney disease, or CKD, where the ability of the patient's kidney to excrete potassium has been compromised. The normal range for serum potassium levels is from about 3.8 mEq/l to 5.0 mEq/L.

Potassium-binding agents can remove potassium from the gastrointestinal tract and reduce the serum potassium level and treat hyperkalemia. In particular, potassium-binding polymers can remove potassium from the gastrointestinal tract and reduce the serum potassium level (U.S. Pat. No. 7,566,799). Various studies show that an increase in serum potassium level increases the aldosterone level and a decrease in serum potassium level decreases the aldosterone level (T. Himathongkam, et al., J. Clin. Endocrinol. Metab. 1975, 41(1):153-159). These studies have shown that a small increase or decrease in serum potassium level can cause a larger change in the aldosterone level. Further, other studies show that an increase in potassium intake can reduce blood pressure (He, F. J., et al., Hypertension 2005, 45:571-574). It has now been discovered, and clinically observed, that lowering of serum potassium levels in patients also lowers blood pressure. This finding was unexpected given that the intended primary benefit of the potassium-binding polymer was to lower serum potassium. The lowering of potassium and blood pressure using a potassium-binding polymer is beneficial in patients with renal impairment, hyperkalemia and hypertension given that these patients are at significant risk of increased morbidity and mortality. Lowering of blood pressure is also beneficial in patients without such co-morbidities who suffer from hypertension.

The potassium-binding agents can be an agent that binds potassium. One class of potassium-binding agents is potassium-binding polymers. Various potassium-binding polymers can be used in the methods described herein including crosslinked cation exchange polymers. The potassium-binding agents can also be zeolites, such as zirconium silicate or zirconium germanate molecular sieves.

The crosslinked cation exchange polymers useful for the methods described herein are in the form of substantially spherical particles. As used herein, the term "substantially" means generally rounded particles having an average aspect ratio of about 1.0 to about 2.0. Aspect ratio is the ratio of the largest linear dimension of a particle to the smallest linear dimension of the particle. Aspect ratios may be easily determined by those of ordinary skill in the art. This definition includes spherical particles, which by definition have an aspect ratio of 1.0.

The particles can have an average aspect ratio of about 1.0, 1.2, 1.4, 1.6, 1.8 or 2.0. The particles may be round or elliptical when observed at a magnification wherein the field of view is at least twice the diameter of the particle.

The crosslinked cation exchange polymer particles have a mean diameter of from about 20 μm to about 200 μm. Specific ranges are where the crosslinked cation exchange particles have a mean diameter of from about 20 μm to about 200 μm, from about 20 μm to about 150 μm, or from about 20 μm to about 125 μm. Other ranges include from about 35 μm to about 150 μm, from about 35 μm to about 125 μm, or from about 50 μm to about 125 μm. Particle sizes, including mean diameters, distributions, etc. can be determined using techniques known to those of skill in the art. For example, U.S. Pharmacopeia (USP) <429> discloses methods for determining particle sizes.

Various crosslinked cation exchange polymer particles also have less than about 4 volume percent of the particles that have a diameter of less than about 10 μm; particularly, less than about 2 volume percent of the particles that have a diameter of less than about 10 μm; more particularly, less than about 1 volume percent of the particles that have a diameter of less than about 10 μm; and even more particularly, less than about 0.5 volume percent of the particles that have a diameter of less than about 10 μm. In other cases, specific ranges are less than about 4 volume percent of the particles that have a diameter of less than about 20 μm; less than about 2 volume percent of the particles that have a diameter of less than about 20 μm; less than about 1 volume percent of the particles that have a diameter of less than about 20 μm; less than about 0.5 volume percent of the particles that have a diameter of less than about 20 μm; less than about 2 volume percent of the particles that have a diameter of less than about 30 μm; less than about 1 volume percent of the particles that have a diameter of less than about 30 μm; less than about 1 volume percent of the particles that have a diameter of less than about 30 μm; less than about 1 volume percent of the particles that have a diameter of less than about 40 μm; or less than about 0.5 volume percent of the particles that have a diameter of less than about 40 μm.

The crosslinked cation exchange polymer can have a particle size distribution wherein not more than about 5 volume % of the particles have a diameter less than about 30 μm (i.e., D(0.05)<30 μm), not more than about 5 volume % of the particles have a diameter greater than about 250 μm (i.e., D(0.05)>250 μm), and at least about 50 volume % of the particles have a diameter in the range from about 70 to about 150 μm.

The particle distribution of the crosslinked cation exchange polymer can be described as the span. The span of the particle distribution is defined as (D(0.9)−D(0.1))/D(0.5), where D(0.9) is the value wherein 90% of the particles have a diameter below that value, D(0.1) is the value wherein 10% of the particles have a diameter below that value, and D(0.5) is the value wherein 50% of the particles have a diameter above that value and 50% of the particles have a diameter below that value as measured by laser diffraction. The span of the particle distribution is typically from about 0.5 to about 1, from about 0.5 to about 0.95, from about 0.5 to about 0.90, or from about 0.5 to about 0.85. Particle size distributions can be measured using Niro Method No. A 8 d (revised September 2005), available from GEA Niro, Denmark, using the Malvern Mastersizer.

Another desirable property that the crosslinked cation exchange polymers may possess is a viscosity when hydrated and sedimented of from about 10,000 Pa·s to about 1,000,000 Pa·s, from about 10,000 Pa·s to about 800,000 Pa·s, from about 10,000 Pa·s to about 600,000 Pa·s, from about 10,000 Pa·s to about 500,000 Pa·s, from about 10,000 Pa·s to about 250,000 Pa·s, or from about 10,000 Pa·s to about 150,000 Pa·s, from about 30,000 Pa·s to about 1,000,000 Pa·s, from about 30,000 Pa·s to about 500,000 Pa·s, or from about 30,000 Pa·s to about 150,000 Pa·s, the viscosity being measured at a shear rate of 0.01 $\sec^{-1}$. This viscosity is measured using a wet polymer prepared by mixing the polymer thoroughly with a slight excess of simulated intestinal fluid (per USP <26>), allowing the mixture to sediment for 3 days at 37° C., and decanting free liquid from the sedimented wet polymer. The steady state shear viscosity of this wet polymer can be determined using a Bohlin VOR Rheometer (available from Malvern Instruments Ltd., Malvern, U.K.) or equivalent with a parallel plate geometry (upper plate of 15 mm diameter and lower plate of 30 mm diameter, and gap between plates of 1 mm) and the temperature maintained at 37° C.

The crosslinked cation exchange polymers may further have a hydrated and sedimented yield stress of from about 150 Pa to about 4000 Pa, from about 150 Pa to about 3000 Pa, from about 150 Pa to about 2500 Pa, from about 150 Pa to about 1500 Pa, from about 150 Pa to about 1000 Pa, from about 150 Pa to about 750 Pa, or from about 150 Pa to about 500 Pa, from about 200 Pa to about 4000 Pa, from about 200 Pa to about 2500 Pa, from about 200 Pa to about 1000 Pa, or from about 200 Pa to about 750 Pa. Dynamic stress sweep measurements (i.e., yield stress) can be made using a Reologica STRESSTECH Rheometer (available from Reologica Instruments AB, Lund, Sweden) or equivalent in a manner known to those of skill in the art. This rheometer also has a parallel plate geometry (upper plate of 15 mm diameter, lower plate of 30 mm diameter, and gap between plates of 1 mm) and the temperature is maintained at 37° C. A constant frequency of 1 Hz with two integration periods can be used while the shear stress is increased from 1 to $10^4$ Pa.

Crosslinked cation exchange polymers useful for the methods described herein also have desirable compressibility and bulk density when in the form of a dry powder. Some of the particles of the crosslinked cation exchange polymers in the dry form have a bulk density of from about 0.8 $g/cm^3$ to about 1.5 $g/cm^3$, from about 0.82 $g/cm^3$ to about 1.5 $g/cm^3$, from about 0.84 $g/cm^3$ to about 1.5 $g/cm^3$, from about 0.86 $g/cm^3$ to about 1.5 $g/cm^3$, from about 0.8 $g/cm^3$ to about 1.2 $g/cm^3$, or from about 0.86 $g/cm^3$ to about 1.2 $g/cm^3$. The bulk density affects the volume of crosslinked cation exchange polymer needed for administration to a patient. For example, a higher bulk density means that a lower volume will provide the same number of grams of crosslinked cation exchange polymer. This lower volume can improve patient compliance by allowing the patient to perceive they are taking a smaller amount due to the smaller volume.

A powder composed of the particles of the crosslinked cation exchange polymer in dry form has a compressibility index of from about 3 to about 15, from about 3 to about 14, from about 3 to about 13, from about 3 to about 12, from about 3 to about 11, from about 5 to about 15, from about 5 to about 13, or from about 5 to about 11. The compressibility index is defined as 100*(TD-BD)/TD, wherein BD and TD are the bulk density and tap density, respectively. The procedure for measuring bulk density and tap density is described below in Example 3. Further, the powder form of the cation exchange polymers settles into its smallest volume more easily than polymers conventionally used to treat hyperkalemia. This makes the difference between the bulk density and the tap density (measured powder density after tapping a set number of times) from about 3% to about 14%, from about 3% to about 13%, from about 3% to about 12%, from about 3% to about 11%, from about 3% to about 10%, from about 5% to about 14%, from about 5% to about 12%, or from about 5% to about 10% of the bulk density.

Generally the potassium-binding polymers in particle form are not absorbed from the gastrointestinal tract. The term "non-absorbed" and its grammatical equivalents is not intended to mean that the entire amount of administered polymer is not absorbed. It is expected that certain amounts of the polymer may be absorbed. Particularly, about 90% or more of the polymer is not absorbed, more particularly about 95% or more is not absorbed, even more particularly about 97% or more is not absorbed, and most particularly about 98% or more of the polymer is not absorbed.

The swelling ratio of the potassium-binding polymers in physiological isotonic buffer, which is representative of the gastrointestinal tract, is typically from about 1 to about 7, particularly from about 1 to about 5, more particularly from about 1 to about 3, and more specifically, from about 1 to about 2.5.

The crosslinked cation exchange polymers can have a swelling ratio of less than 5, less than about 4, less than about 3, less than about 2.5, or less than about 2. As used herein, "swelling ratio" refers to the number of grams of solvent taken up by one gram of otherwise non-solvated crosslinked polymer when equilibrated in an aqueous environment. When more than one measurement of swelling is taken for a given polymer, the mean of the measurements is taken to be the swelling ratio. The polymer swelling can also be calculated by the percent weight gain of the otherwise non-solvated polymer upon taking up solvent. For example, a swelling ratio of 1 corresponds to polymer swelling of 100%.

Crosslinked cation exchange polymers having advantageous surface morphology are polymers in the form of substantially spherical particles with a substantially smooth surface. A substantially smooth surface is a surface wherein the average distance from the peak to the valley of a surface feature determined at random over several different surface features and over several different particles is less than about 2 μm, less than about 1 μm, or less than about 0.5 μm. Typically, the average distance between the peak and the valley of a surface feature is less than about 1 μm.

The surface morphology can be measured using several techniques including those for measuring roughness. Roughness is a measure of the texture of a surface. It is quantified by the vertical deviations of a real surface from its ideal form. If these deviations are large, the surface is rough; if they are small the surface is smooth. Roughness is typically considered to be the high frequency, short wavelength component of a measured surface. For example, roughness may be measured using contact or non-contact methods. Contact methods involve dragging a measurement stylus across the surface; these instruments include profilometers and atomic force microscopes (AFM). Non-contact methods include interferometry, confocal microscopy, electrical capacitance and electron microscopy. These methods are described in more detail in Chapter 4: Surface Roughness and Microtopography by L. Mattson in Surface Characterization, ed. by D. Brune, R. Hellborg, H. J. Whitlow, O. Hunderi, Wiley-VCH, 1997.

For three-dimensional measurements, the probe is commanded to scan over a two-dimensional area on the surface. The spacing between data points may not be the same in both directions. In this way, a side view of the surface can be obtained and the relief of the surface can be measured.

Surface roughness can be controlled in a number of ways. For example, three approaches were determined for preparing poly(α-fluoroacrylate) particles having a smoother surface. The first approach was to include a solvent that was an acceptable solvent for the monomers and the polymeric product. The second approach was to decrease the solvation of the organic phase in the aqueous phase by a salting out process. The third approach was to increase the hydrophobicity of the starting fluoroacrylate monomer. These approaches are described in more detail in Examples 4-7.

Dosing regimens for chronic treatment of hyperkalemia can increase compliance by patients, particularly for crosslinked cation exchange polymers that are taken in gram quantities. The present invention is also directed to methods of chronically removing potassium from a mammal in need thereof, and in particular chronically treating hyperkalemia with a potassium binder that is a crosslinked aliphatic carboxylic polymer, and preferably a salt of such polymer stabilized with a linear polyol, wherein the polymer is in the form of a substantially spherical particle.

Thus, the invention is directed to methods of treating hypertension or hyperkalemia or kidney disease in a patient in need thereof, the method comprising administering an effective amount of a potassium-binding agent, to the patient. In particular, the invention is directed to methods of treating hypertension and hyperkalemia in a patient in need thereof. In particular also, the invention is directed to methods of treating kidney disease and hyperkalemia in a patient in need thereof.

In the methods described here, the potassium-binding agent can be 2-fluoroacrylate-divinylbenzene-1,7-octadiene copolymer, crosslinked in the salt or acid form.

The methods of treating hypertension or kidney disease can include chronic administration of the potassium-binding agent. The potassium-binding agent exhibits long-term tolerability, long-term safety, and/or long-term efficacy in the patient. The long-term tolerability, long-term safety, and long-term efficacy are observed over treatment periods of 12, 16, 20, 24, 28, 32, 36, 40, 44, 48, 52, or more weeks. The treatment period can also be 2 years, 3 years, 4 years, 5 years, or more. Particularly, the potassium-binding agent can be administered to the patient daily for more than 8 weeks or daily for more than one year.

In particular, the 2-fluoroacrylate-divinylbenzene-1,7-octadiene copolymer crosslinked in the salt or acid form exhibits long-term tolerability, long-term safety, and/or long-term efficacy in the patient. The long-term tolerability, long-term safety, and long-term efficacy are observed over treatment periods of 12, 16, 20, 24, 28, 32, 36, 40, 44, 48, 52, or more weeks. The treatment period can also be 2 years, 3 years, 4 years, 5 years, or more. Particularly, the 2-fluoroacrylate-divinylbenzene-1,7-octadiene copolymer crosslinked in the salt or acid form can be administered to the patient daily for more than 8 weeks or daily for more than one year.

The methods of treating hypertension and hyperkalemia can also reduce the patient's systolic blood pressure by 5, 6, 7, 8 mmHg as compared to the patient's systolic blood pressure before treatment with the potassium-binding agent, and/or reduce the patient's diastolic blood pressure 2, 3, 4, 5, 6 mmHg as compared to the patient's diastolic blood pressure before treatment with potassium-binding agent.

The methods of treating hypertension and hyperkalemia can also reduce the patient's systolic blood pressure by 9, 10, 11, 12, 13, 14, 15, 16, 17 mmHg or more as compared to the patient's systolic blood pressure before treatment with potassium-binding agent, and/or reduce the patient's diastolic blood pressure 7, 8, 9, 10, 11, 12, 13 mmHg or more as compared to the patient's diastolic blood pressure before treatment with potassium-binding agent.

The methods of treating hypertension and hyperkalemia can also reduce the patient's systolic blood pressure by at least 6, 7, 8, 9, 10, 11, 12, or more percent as compared to the patient's systolic blood pressure before treatment with potassium-binding agent, and/or the patient's diastolic blood pressure is reduced by at least 8, 9, 10, 11, 12, 13, 14, 15, or more percent as compared to the patient's diastolic blood pressure before treatment with potassium-binding agent.

The potassium-binding agent can be administered to a patient having a systolic blood pressure greater than 130 mmHg or ranging from 130 to 200 mmHg, 135 to 200 mmHg, 140 to 200 mmHg, 145 to 200 mmHg, or 150 to 180 mmHg before treatment with potassium-binding agent.

The potassium-binding agent can be administered to a patient having a systolic blood pressure greater than 143 mmHg or ranging from 143 to 200 mmHg or 143 to 180 mmHg before treatment with potassium-binding agent.

The systolic blood pressure of the patient can be maintained below 130, 135, or 140 mmHg over at least 90% of the period of treatment with potassium-binding agent. The diastolic blood pressure of the patient can be maintained at below 80, 85, or 90 mmHg over at least 90% of the period of treatment with potassium-binding agent.

The methods of treating hypertension can include administering an effective amount of potassium-binding agent to a heart failure patient, a type 2 diabetes mellitus patient, and/or a chronic kidney disease patient in need of hypertension treatment, the patient optionally being treated with an effective amount of a renin-angiotensin-aldosterone system (RAAS) agent.

The methods of treatment of hypertension can be administered to a patient suffering from chronic kidney disease, heart failure, type 2 diabetes mellitus or a combination thereof.

The potassium-binding agent can be administered to a patient that is not being treated with an aldosterone antagonist. Particularly, the patient is not being treated with spironolactone.

The methods of treating hypertension can include administration of potassium-binding agent to a patient that does not have another condition that causes hypertension such as Type 2 diabetes, chronic kidney disease, chronic heart failure or a combination thereof. Particularly, the patient does not have type 2 diabetes mellitus, or the patient that does not have chronic kidney disease (CKD).

The methods of treating hypertension can include administration of potassium-binding agent to a patient that does not have Class II or Class III heart failure (HF).

The methods of treating hypertension can also include administration of potassium-binding agent to a patient that is not being treated with a heart failure therapy; the heart failure therapy can be an angiotensin converting enzyme inhibitor (ACEI), an angiotensin receptor blocker (ARB), a beta blocker (BB), or a combination thereof.

The patients receiving the treatment methods of the invention need not be treated with an antihypertensive agent comprising a diuretic, a calcium channel blocker, an alpha blocker, a nervous system inhibitor, a vasodilator, an angiotensin converting enzyme inhibitor (ACEI), an angiotensin receptor blocker (ARB), a beta blocker (BB), or a combination thereof.

The methods of treating hypertension of the invention can be administered to patients that are normokalemic. Normokalemic patients have a serum potassium level of 3.5 to 5.0 mEq/L.

The present invention is directed to methods of treating hyperkalemia in a chronic kidney disease patient in need thereof optionally being treated with an effective amount of a renin-angiotensin-aldosterone system (RAAS) agent. The methods generally comprise administering an effective amount of a potassium-binding polymer to the patient to increase or stabilize the patient's kidney function.

The present invention is directed to methods of treating chronic kidney disease in a patient in need thereof optionally being treated with an effective amount of a renin-angiotensin-aldosterone system (RAAS) agent. The methods generally comprise administering an effective amount of a potassium-binding polymer to the patient to increase or stabilize the patient's kidney function.

In the methods of treating kidney disease, there are several ways in which the methods can exhibit an increase to or stabilization of the patient's kidney function, such as by decreasing the patient's serum creatinine level as compared to the patient's serum creatinine level before treatment with a potassium-binding agent; increasing the time to progression of end stage renal disease as compared to a chronic kidney disease patient optionally treated with a RAAS agent but not treated with a potassium-binding agent; increasing survival as compared to a chronic kidney disease patient optionally treated with a RAAS agent but not treated with a potassium-binding agent; and/or increasing or stabilizing estimated glomerular filtration rate (eGFR) as compared to the patient's eGFR before treatment with a potassium-binding agent.

For all of these methods of treatment including treating hypertension, hyperkalemia, chronic kidney disease, end stage renal disease, etc. the potassium-binding agent can be a potassium-binding polymer.

For the methods of treatment described herein, the potassium-binding polymer can be a crosslinked cation exchange polymer.

For the methods of treatment described herein, the potassium-binding polymer can be an aliphatic crosslinked cation exchange polymer.

For the methods of treatment described herein, the potassium-binding polymer can be 2-fluoroacrylate-divinylbenzene-1,7-octadiene copolymer crosslinked in the salt or acid form.

For the methods of treatment described herein, the potassium-binding agent can be a zirconium silicate or a zirconium germanate molecular sieve.

For the methods of treatment described herein, the potassium-binding agent can be $Na_{2.19}ZrSi_{3.01}O_{9.11} \cdot 2.71\ H_2O$.

As detailed in Example 2, a Phase II clinical study conducted in Type 2 diabetes mellitus (T2DM) patients with chronic kidney disease (CKD) Phase ¾ is instructive. All patients are treated with a RAAS inhibitor, and about 40% of the patients also have heart failure (HF). And, endpoints measure changes from baseline at various time points. The trial is an 8-week, open-label, randomized, dose ranging study to determine the optimal starting dose(s) of 2-fluoroacrylate-divinylbenzene-1,7-octadiene copolymer crosslinked in the salt or acid form. In addition, the study contains a 44-week long-term safety extension component, in order to collect 1-year safety data that will support chronic use of 2-fluoroacrylate-divinylbenzene-1,7-octadiene copolymer crosslinked in the salt or acid form. Patients with normal serum $K^+$ levels of 4.3–5.0 mEq/L were enrolled in a run-in period during which they received the maximum labeled dose of losartan and/or additional spironolactone as needed. Patients with serum $K^+$ levels>5.0 mEq/L at baseline entered the study without a run-in period (data from some of these patients are shown in FIGS. 6-9). For treatment of hyperkalemia (serum $K^+$>5.0 mEq/L), two potassium strata were chosen (stratum 1=serum $K^+$>5.0–5.5 mEq/L; stratum 2=serum $K^+$>5.5–<6.0 mEq/L), based on the National Kidney Foundation Kidney Disease Outcomes Quality Initiative Guideline 11 (KDOQI, 2004) definition of hyperkalemia and serum potassium cut-off points for ACEI/ARB dose modification.

This Phase II Study was enrolled with a total of 306 subjects treated for an average duration of 9.5 months. All subjects completed the trial, with 266 subjects completing 8 weeks, 226 subjects completing 6 months and 197 patients completing one year.

Several key observations can be made. Looking at interim data, and a statistically significant number of the 182 patients had an albumin creatinine ratio (ACR) of ≥30 mg/g and others had an ACR of >300 mg/g and an estimated glomerular filtration rate (eGFR) of 15 to 44 mL/min/1.73 $m^2$ at baseline. As shown in FIG. 1, for all of these patients, the patient's serum potassium concentration decreased from an average of 5.27 mEq/L at baseline to an average of 4.57 mEq/L at 24 weeks. For patients having an ACR≥30 mg/g, the patient's serum potassium concentration decreased from an average of 5.28 mEq/L at baseline to an average of 4.60 mEq/L at 24 weeks. For patients having an ACR>300 mg/g, the patient's serum potassium concentration decreased from an average of 5.35 mEq/L at baseline to an average of 4.65 mEq/L at 24 weeks. For patients having an eGFR of 15 to 44 mL/min/1.73 $m^2$, the patient's serum potassium concentration decreased from an average of 5.33 mEq/L at baseline to an average of 4.59 mEq/L at 24 weeks.

Figure 2:
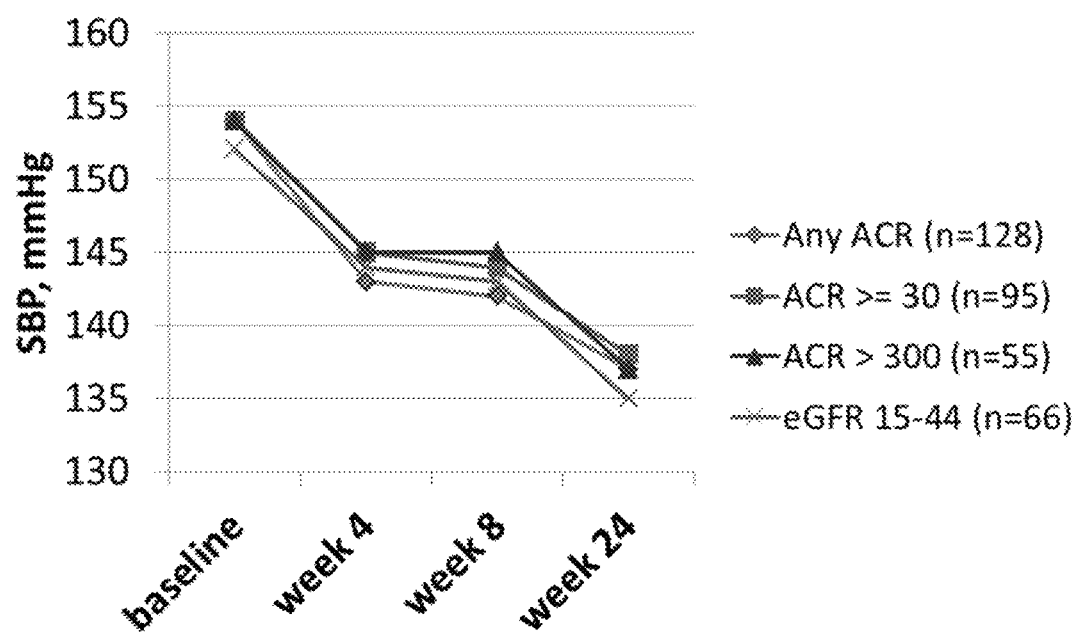
FIG. 2 is a graph of the systolic blood pressure (SBP) in mmHg versus time of treatment for patients having been treated for six months with the protocol described in Example 2 and having any albumin creatinine ratio (ACR), an ACR≥30, and ACR>300 and an estimated glomerular filtration rate (eGFR) of 15-44 mL/min/1.73 $m^2$.

As shown in FIG. 2, for all of these patients, the patient's systolic blood pressure decreased from an average of 154 at baseline to an average of 137 at 24 weeks; for patients having an ACR≥30 mg/g, the patient's systolic blood pressure decreased from an average of 154 at baseline to an average of 138 at 24 weeks; for patients having an ACR>300 mg/g, the patient's systolic blood pressure decreased from an average of 154 at baseline to an average of 137 at 24 weeks; and for patients having an eGFR of 15 to 44 mL/min/1.73 $m^2$, the patient's systolic blood pressure decreased from an average of 152 at baseline to an average of 135 at 24 weeks.

Figure 3:
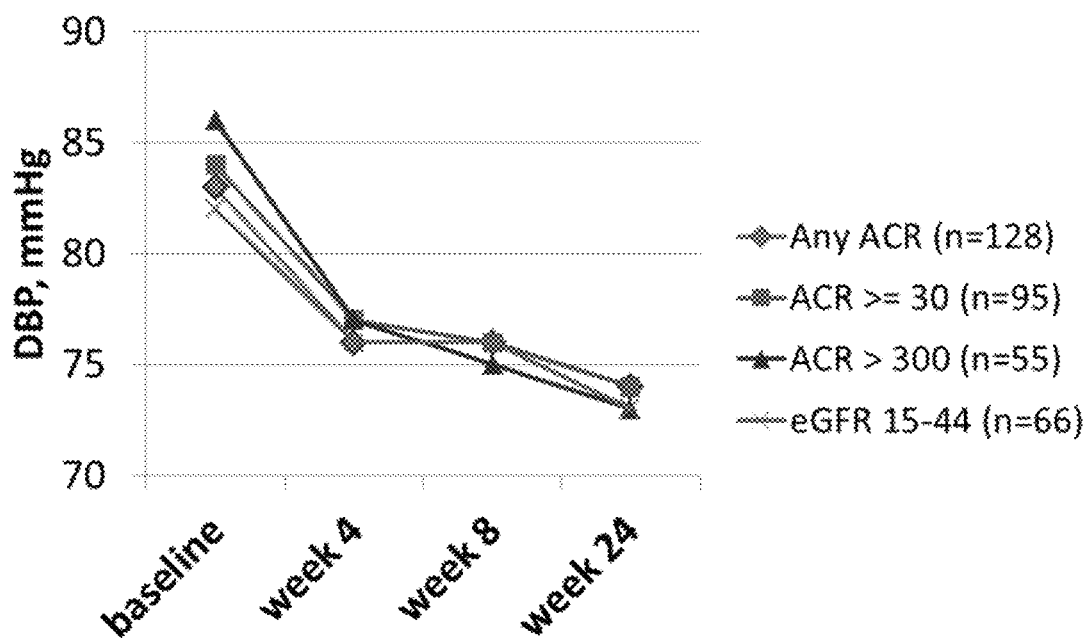
FIG. 3 is a graph of the diastolic blood pressure (DBP) in mmHg versus time of treatment for patients having been treated for six months with the protocol described in Example 2 and having any albumin creatinine ratio (ACR), an ACR≥30, and ACR>300 and an estimated glomerular filtration rate (eGFR) of 15-44 mL/min/1.73 $m^2$.

As shown in FIG. 3, for all of these patients, the patient's diastolic blood pressure decreased from an average of 83 at baseline to an average of 74 at 24 weeks; for patients having an ACR≥30 mg/g, the patient's diastolic blood pressure decreased from an average of 84 at baseline to an average of 74 at 24 weeks; for patients having an ACR>300 mg/g, the patient's diastolic blood pressure decreased from an average of 86 at baseline to an average of 73 at 24 weeks; and or patients having an eGFR of 15 to 44 mL/min/1.73 $m^2$, the patient's diastolic blood pressure decreased from an average of 82 at baseline to an average of 73 at 24 weeks.

Figure 4:
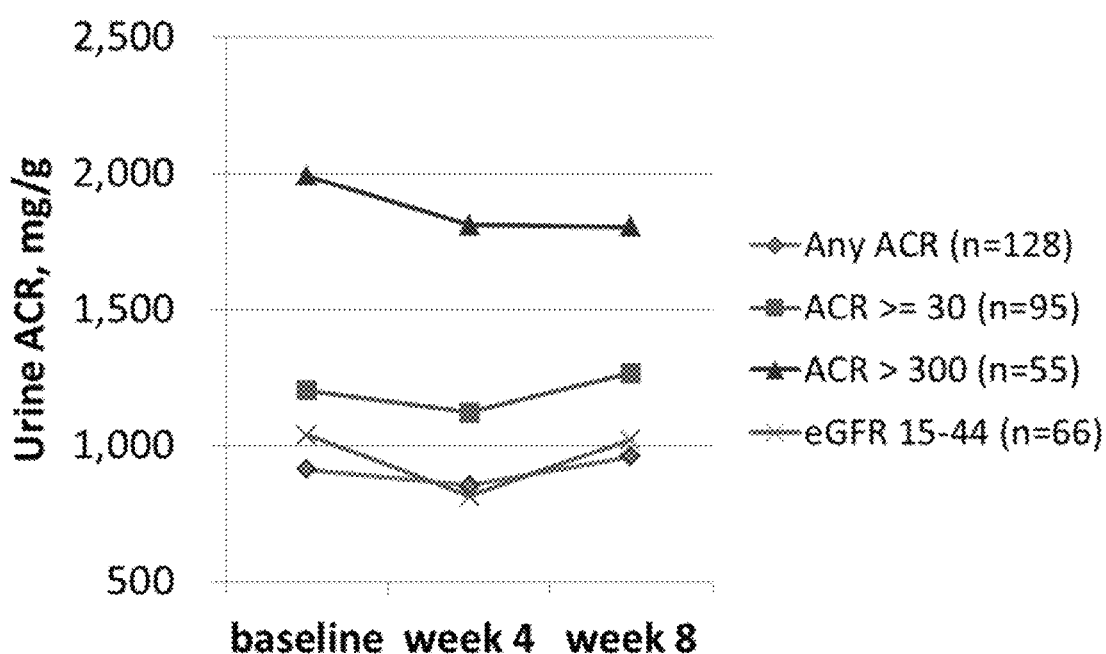
FIG. 4 is a graph of the urine ACR in mg/g versus time of treatment for patients having been treated for six months with the protocol described in Example 2 and having any albumin creatinine ratio (ACR), an ACR≥30, and ACR>300 and an estimated glomerular filtration rate (eGFR) of 15-44 mL/min/1.73 $m^2$.

As shown in FIG. 4, for the patients in all groups and each group separately (e.g., ACR of ≥30 mg/g, ACR of >300 mg/g, eGFR of 15 to 44 mL/min/1.73 $m^2$), the ACR did not significantly change over the 24 week treatment period.

Figure 5:
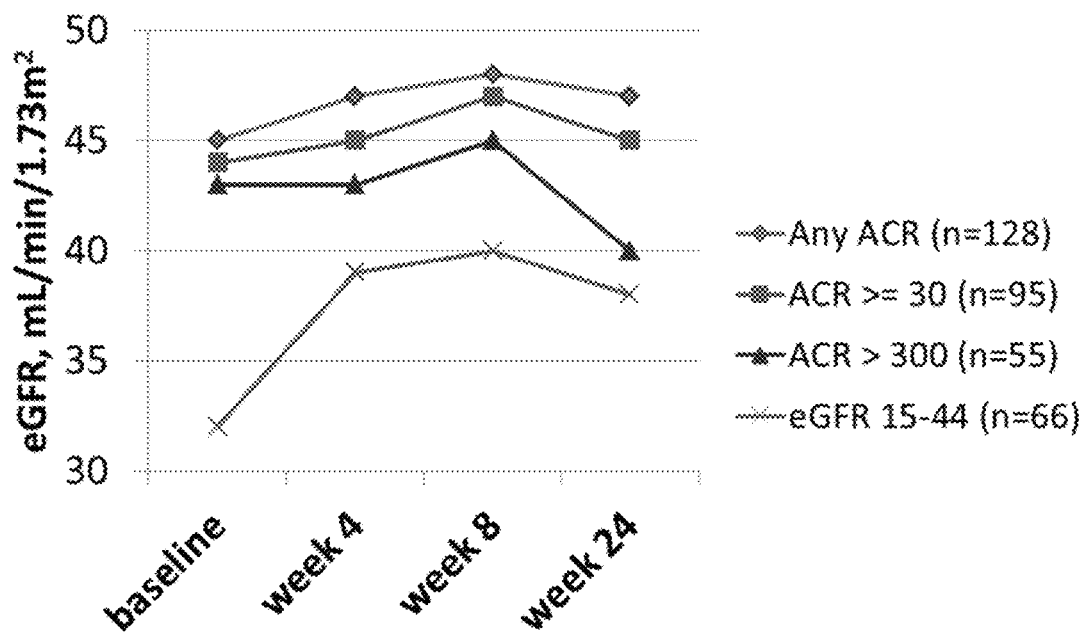
FIG. 5 is a graph of the eGFR in mL/min/1.73 $m^2$ versus time of treatment for patients having been treated for six months with the protocol described in Example 2 and having any albumin creatinine ratio (ACR), an ACR≥30, and ACR>300 and an estimated glomerular filtration rate (eGFR) of 15-44 mL/min/1.73 $m^2$.

As shown in FIG. 5, for patients having an eGFR of 15 to 44 mL/min/1.73 m², the patient's eGFR increased from an average of 32 mL/min/1.73 m² at baseline to an average of 38 mL/min/1.73 m² at 24 weeks. This increase in eGFR for these patients was statistically significant.

Figure 6:
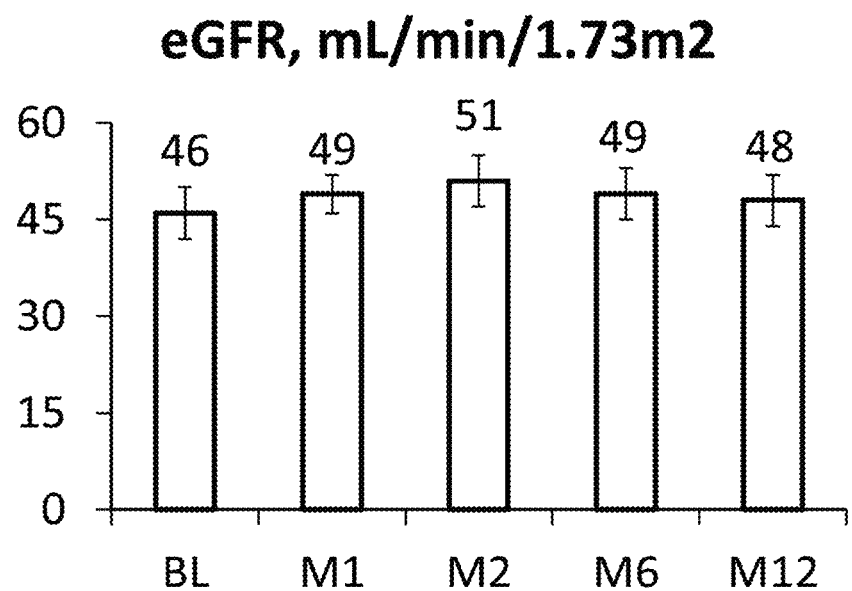
FIG. 6 is a graph of eGFR versus time of treatment for a cohort of patients having pre-existing hyperkalemia on a stable dose of a RAAS inhibitor that came to the trial without a run-in period that were treated for twelve months as described in Example 2. For FIGS. 6-9, the data is presented at baseline (BL), one month (M1), two months (M2), six months (M6), and twelve months (M12).
Figure 7:
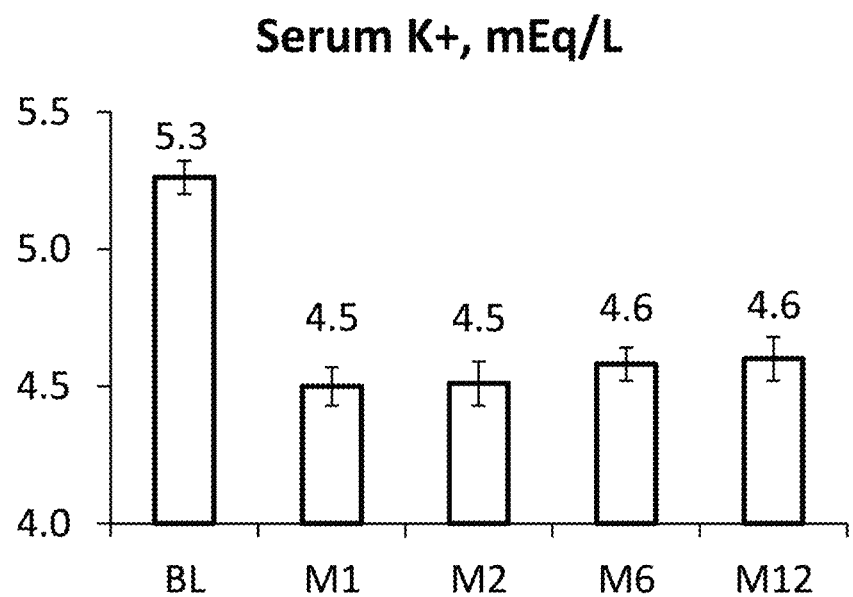
FIG. 7 is a graph of serum potassium versus time of treatment for a cohort of patients having pre-existing hyperkalemia on a stable dose of a RAAS inhibitor that came to the trial without a run-in period that were treated for twelve months with as described in Example 2.
Figure 8:
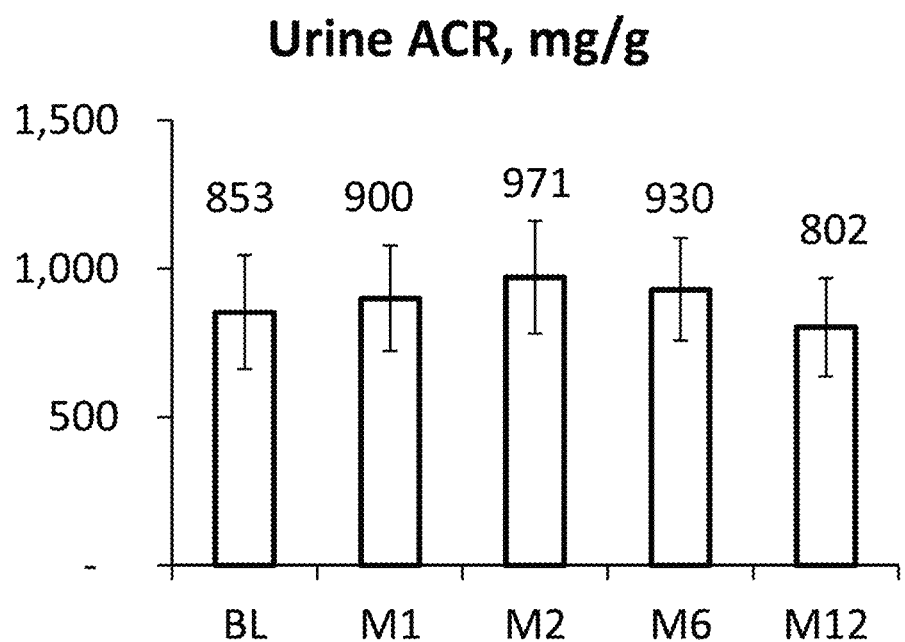
FIG. 8 is a graph of urine ACR versus time of treatment for a cohort of patients having pre-existing hyperkalemia on a stable dose of a RAAS inhibitor that came to the trial without a run-in period that were treated for twelve months as described in Example 2.
Figure 9:
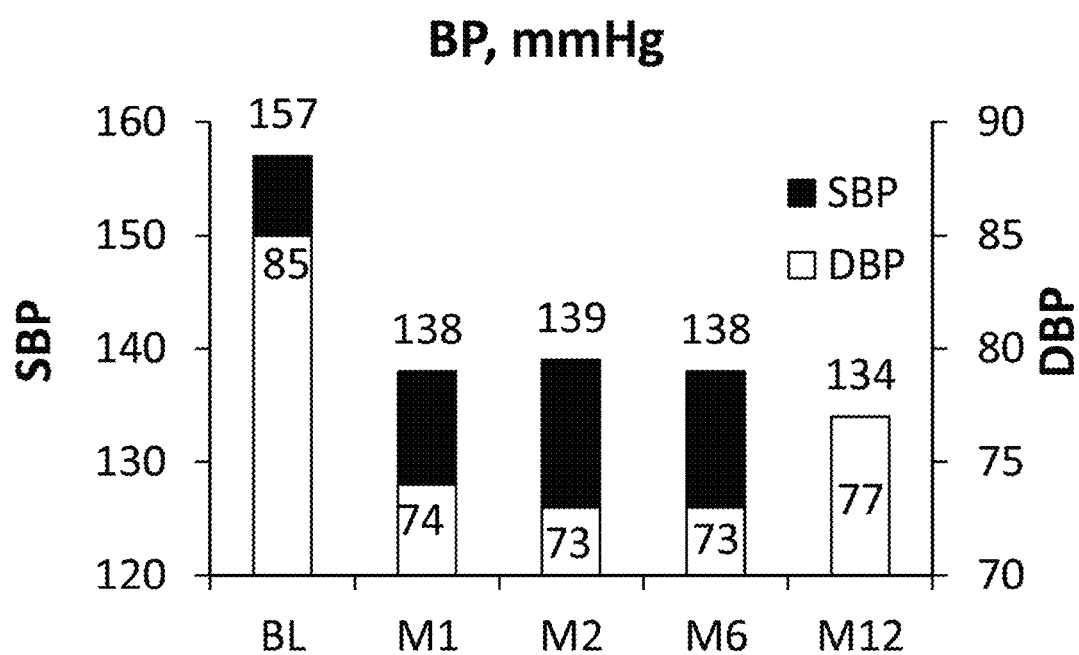
FIG. 9 is a graph of systolic and diastolic blood pressure versus time of treatment for a cohort of patients having pre-existing hyperkalemia on a stable dose of a RAAS inhibitor that came to the trial without a run-in period that were treated for twelve months as described in Example 2.

As described above, FIGS. 6-9 show data from a certain cohort of patients with pre-existing hyperkalemia taking a stable dose of a RAAS inhibitor that came into the trial without a run-in period. As shown in FIG. 6, the average of these patients' eGFR of 46 mL/min/1.73 m² at baseline did not decrease over time, as can be expected in these patients. Further data suggests that in a subset of patients, the eGFR appears to increase at one year. As shown in FIG. 7, the average of these patients' serum potassium level decreased significantly from 5.3 mEq/L at baseline into the normal range (to 4.6 mEq/L) at 12 months. As shown in FIG. 8, the average of these patients' urine ACR of 853 mg/g at baseline was not significantly different from the average of the patients' urine ACR at any other time point. As shown in FIG. 9, the average of these patients' systolic blood pressure decreased from 157 mmHg to 134 mmHg and the average of these patients' diastolic blood pressure decreased from 85 mmHg to 77 mmHg.

Additional observations can be made from the study results. First, the starting serum potassium is a factor in determining efficacy of 2-fluoroacrylate-divinylbenzene-1, 7-octadiene copolymer crosslinked in the salt or acid form. The interim analysis of the 8-week Treatment Initiation Period performed for 304 subjects showed a mean decrease in serum potassium from baseline to week 8 in subjects in the upper serum potassium stratum (Stratum 2: serum $K^+$>5.5 to <6.0 mEq/L) that was approximately twice that in subjects in the lower serum potassium stratum (Stratum 1: serum $K^+$>5.0 to 5.5 mEq/L) (−0.90 mEq/L versus −0.47 mEq/L, respectively). This baseline effect was seen within the first week on treatment. Second, underlying RAAS inhibitor treatment does not appear to influence the efficacy of 2-fluoroacrylate-divinylbenzene-1,7-octadiene copolymer crosslinked in the salt or acid form. Third, the efficacy of 2-fluoroacrylate-divinylbenzene-1,7-octadiene copolymer crosslinked in the salt or acid form appears to be independent of comorbidities.

The potassium-binding polymers can be crosslinked cation exchange polymers derived from at least one crosslinker and at least one monomer containing acid groups in their protonated or ionized form, such as sulfonic, sulfuric, carboxylic, phosphonic, phosphoric, or sulfamic groups, or combinations thereof. In general, the fraction of ionization of the acid groups of the polymers used in this invention is greater than about 75% at the physiological pH (e.g., about pH 6.5) in the colon and the potassium binding capacity in vivo is greater than about 0.6 mEq/gram, more particularly greater than about 0.8 mEq/gram and even more particularly greater than about 1.0 mEq/gram. Generally the ionization of the acid groups is greater than about 80%, more particularly it is greater than about 90%, and most particularly it is about 100% at the physiological pH of the colon (e.g., about pH 6.5).

The acid containing polymers can contain more than one type of acid group. In other instances, the acid containing polymers are administered in their substantially anhydrous or salt form and generate the ionized form when contacted with physiological fluids. Representative structural units of these potassium-binding polymers are shown in Table 1 wherein the asterisk at the end of a bond indicates that bond is attached to another structural unit or to a crosslinking unit.

TABLE 1

Examples of cation exchange structural units—structures and theoretical binding capacities

| Structure | Molar mass per charge | Theoretical capacity | Fraction of titrable H @pH 3 | Fraction of titrable H @pH 6 | Expected Capacity @pH 3 | Expected Capacity @pH 6 |
|---|---|---|---|---|---|---|
| (carboxylate) | 71 | 14.1 | 0.05 | .35 | 0.70 | 4.93 |
| (fluoro-carboxylate) | 87 | 11.49 | 0.2 | 0.95 | 2.3 | 10.92 |
| (phosphonate) | 53 | 18.9 | 0.25 | 0.5 | 4.72 | 9.43 |
| (bis-phosphonate) | 47.5 | 21.1 | 0.25 | 0.5 | 5.26 | 10.53 |

TABLE 1-continued
Examples of cation exchange structural units—structures and theoretical binding capacities
| | Molar mass per charge | Theoretical capacity | Fraction of titrable H @pH 3 | Fraction of titrable H @pH 6 | Expected Capacity @pH 3 | Expected Capacity @pH 6 |
|---|---|---|---|---|---|---|
| 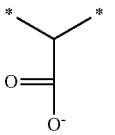 | 57 | 17.5 | 0.1 | 0.5 | 1.75 | 8.77 |
| 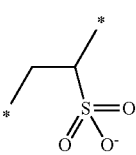 | 107 | 9.3 | 1 | 1 | 9.35 | 9.35 |
| 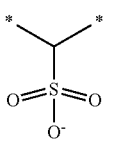 | 93 | 10.8 | 1 | 1 | 10.75 | 10.75 |
| 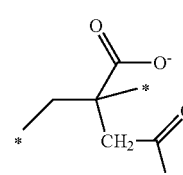 | 63 | 15.9 | 0 | 0.4 | 0 | 6.35 |
| 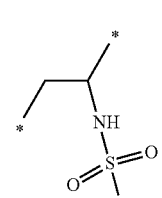 | 125 | 8 | 1 | 1 | 8 | 8 |
| 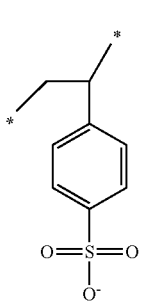 | 183 | 5.5 | 1 | 1 | 5.46 | 5.46 |
| 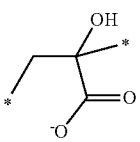 | 87 | 11.49 | .1 | .6 | 1.14 | 6.89 |

Other suitable cation exchange polymers contain repeat units having the following structures:

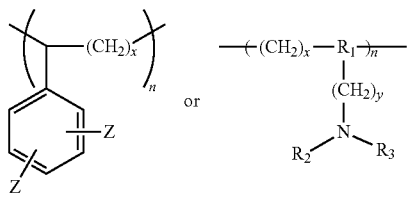

wherein $R_1$ is a bond or nitrogen, $R_2$ is hydrogen or Z, $R_3$ is Z or —$CH(Z)_2$, each Z is independently $SO_3H$ or $PO_3H$, x is 2 or 3, and y is 0 or 1, n is about 50 or more, more particularly n is about 100 or more, even more particularly n is about 200 or more, and most particularly n is about 500 or more.

Sulfamic (i.e. when Z=$SO_3H$) or phosphoramidic (i.e. when Z=$PO_3H$) polymers can be obtained from amine polymers or monomer precursors treated with a sulfonating agent such as sulfur trioxide/amine adducts or a phosphonating agent such as $P_2O_5$, respectively. Typically, the acidic protons of phosphonic groups are exchangeable with cations, like sodium or potassium, at pH of about 6 to about 7.

Suitable phosphonate monomers include vinyl phosphonate, vinyl-1,1-bis phosphonate, and ethylenic derivatives of phosphonocarboxylate esters, oligo(methylenephosphonates), and hydroxyethane-1,1-diphosphonic acid. Methods of synthesis of these monomers are well known in the art.

The cation exchange structural units and repeat units containing acid groups as described above are crosslinked to form the crosslinked cation exchange polymers of the invention. Representative crosslinking monomers include those shown in Table 2.

TABLE 2

Crosslinker Abbreviations and Structures

| Abbreviation | Chemical name | Structure | Molecular Weight |
|---|---|---|---|
| X-V-1 | ethylenebisacrylamide | 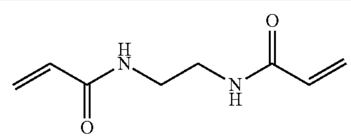 | 168.2 |
| X-V-2 | N,N'-(ethane-1,2-diyl)bis(3-(N-vinylformamido) propanamide) | 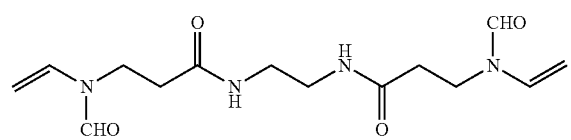 [SMILES: C=CN(C=O)CCC(=O)NCCNC(=O)CCN(C=C)C=O] | 310.36 |
| X-V-3 | N,N'-(propane-1,3-diyl)-diethenesulfonamide | 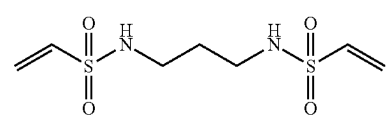 | 254.33 |
| X-V-4 | N,N'-bis(vinylsulfonylacetyl) ethylene diamine | 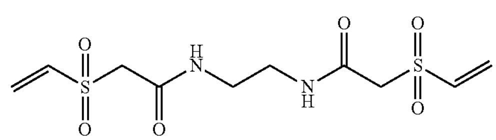 [SMILES: C=CS(=O)(=O)CC(=O)NCCNC(=O)CS(=O)(=O)C=C] | 324.38 |
| X-V-5 | 1,3-bis(vinylsulfonyl) 2-propanol | 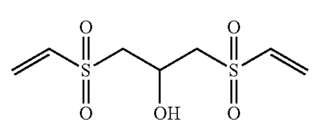 | 240.3 |
| X-V-6 | vinylsulfone | 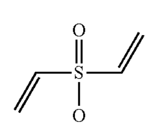 | 118.15 |
| X-V-7 | N,N'-methylenebisacrylamide | 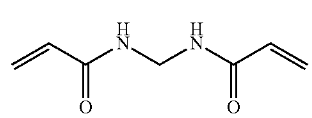 | 154.17 |
| ECH | epichlorohydrin | 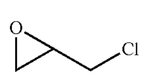 | 92.52 |

TABLE 2-continued

Crosslinker Abbreviations and Structures

| Abbreviation | Chemical name | Structure | Molecular Weight |
|---|---|---|---|
| DVB | Divinyl benzene | 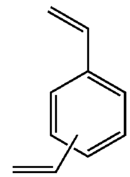 | 130.2 |
| ODE | 1,7-octadiene | 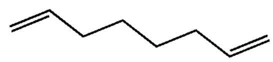 | 110.2 |
| HDE | 1,5-hexadiene | 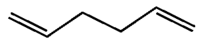 | 82.15 |

The ratio of repeat units to crosslinker can be chosen by those of skill in the art based on the desired physical properties of the polymer particles. For example, the swelling ratio can be used to determine the amount of crosslinking based on the general understanding of those of skill in the art that as crosslinking increases, the swelling ratio generally decreases.

The amount of crosslinker in the polymerization reaction mixture can be in the range of 3 wt. % to 15 wt. %, more specifically in the range of 5 wt. % to 15 wt. % and even more specifically in the range of 8 wt. % to 12 wt. %, based on the total weight of the monomers and crosslinkers added to the polymerization reaction. Crosslinkers can include one or a mixture of those in Table 2.

The crosslinked cation exchange polymer can also include a pKa-decreasing group, preferably an electron-withdrawing substituent, located adjacent to the acid group, preferably in the alpha or beta position of the acid group. The preferred position for the electron-withdrawing group is attached to the carbon atom alpha to the acid group. Generally, electron-withdrawing substituents are a hydroxyl group, an ether group, an ester group, an acid group, or a halide atom. More preferably, the electron-withdrawing substituent is a halide atom. Most preferably, the electron-withdrawing group is fluoride and is attached to the carbon atom alpha to the acid group. Acid groups are carboxylic, phosphonic, phosphoric, or combinations thereof.

Other particularly preferred polymers result from the polymerization of alpha-fluoro acrylic acid, difluoromaleic acid, or an anhydride thereof. Monomers for use herein include α-fluoroacrylate and difluoromaleic acid, with α-fluoroacrylate being most preferred. This monomer can be prepared from a variety of routes, see for example, Gassen et al, J. Fluorine Chemistry, 55, (1991) 149-162, K F Pittman, C. U., M. Ueda, et al. (1980). Macromolecules 13(5): 1031-1036. Difluoromaleic acid is prepared by oxidation of fluoroaromatic compounds (Bogachev et al, Zhurnal Organisheskoi Khimii, 1986, 22(12), 2578-83), or fluorinated furan derivatives (See U.S. Pat. No. 5,112,993). A mode of synthesis of α-fluoroacrylate is given in EP 415214.

Further, the potassium-binding polymer can be 2-fluoroacrylate-divinylbenzene-1,7-octadiene copolymer, crosslinked in the salt or acid form. Particularly, the 2-fluoroacrylate-divinylbenzene-1,7-octadiene copolymer crosslinked in the salt or acid form is in the salt form. The salt form comprises the sodium, calcium, magnesium, ammonium, or a combination thereof; preferably, the salt form comprises the calcium salt form.

Also, the 2-fluoroacrylate-divinylbenzene-1,7-octadiene copolymer, crosslinked in the salt form can be stabilized with a linear polyol. Particularly, the 2-fluoroacrylate-divinylbenzene-1,7-octadiene copolymer, crosslinked in the salt form can be stabilized with 10 wt. % to about 40 wt. % of a linear polyol based on the total weight of the composition.

A linear polyol is added to the composition containing the salt of a potassium-binding polymer (e.g., 2-fluoroacrylate-divinylbenzene-1,7-octadiene copolymer, crosslinked in the salt form) in an amount effective to stabilize the polymer salt, and generally from about 10 wt. % to about 40 wt. % linear polyol based on the total weight of the composition.

The linear polyol is preferably a linear sugar (i.e., a linear sugar alcohol). The linear sugar alcohol is preferably selected from the group consisting of D-(+)arabitol, erythritol, glycerol, maltitol, D-mannitol, ribitol, D-sorbitol, xylitol, threitol, galactitol, isomalt, iditol, lactitol and combinations thereof, more preferably selected from the group consisting of D-(+)arabitol, erythritol, glycerol, maltitol, D-mannitol, ribitol, D-sorbitol, xylitol, and combinations thereof, and most preferably selected from the group consisting of xylitol, sorbitol, and a combination thereof.

Preferably, the pharmaceutical composition contains from about 15 wt. % to about 35 wt. % stabilizing polyol based on the total weight of the composition. This linear polyol concentration can be sufficient to reduce the release of fluoride ion from the cation exchange polymer upon storage as compared to an otherwise identical composition containing no stabilizing polyol at the same temperature and storage time.

Further, the potassium-binding polymer can be a crosslinked cation exchange polymer comprising units having Formulae 1, 2, and 3 as represented by the following structures:

Formula 1

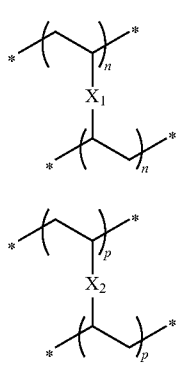

Formula 2

Formula 3 wherein $R_1$ and $R_2$ are independently selected from hydrogen, alkyl, cycloalkyl, or aryl; $A_1$ is carboxylic, phosphonic, or phosphoric in its salt or acid form; $X_1$ is arylene; $X_2$ is alkylene, an ether moiety or an amide moiety, m is in the range of from about 85 to about 93 mol %, n is in the range of from about 1 to about 10 mol % and p is in the range of from about 1 to about 10 mol % calculated based on the ratio of monomers and crosslinkers added to the polymerization mixture.

When $X_2$ is an ether moiety, the ether moiety can be —$(CH_2)_d$—O—$(CH_2)_e$— or —$(CH_2)_d$—O—$(CH_2)_e$—O—$(CH_2)_d$—, wherein d and e are independently an integer of 1 through 5.

Preferably, d is an integer from 1 to 2 and e is an integer from 1 to 3.

When $X_2$ is an amide moiety, the amide moiety can be —C(O)—NH—$(CH_2)_p$—NH—C(O)— wherein p is an integer of 1 through 8. Preferably, p is an integer of 4 to 6.

The unit corresponding to Formula 2 can be derived from a difunctional crosslinking monomer having the formula $CH_2$=CH—$X_1$—CH=$CH_2$ wherein $X_1$ is as defined in connection with Formula 2.

The unit corresponding to Formula 3 can be derived from a difunctional crosslinking monomer having the formula $CH_2$=CH—$X_2$—CH=$CH_2$ wherein $X_2$ is as defined in connection with Formula 3.

In connection with Formula 1, $R_1$ and $R_2$ are hydrogen and $A_1$ is carboxylic.

In connection with Formula 2, $X_1$ is an optionally substituted phenylene, and preferably phenylene.

In connection with Formula 3, $X_2$ is optionally substituted ethylene, propylene, butylene, pentylene, or hexylene; more specifically, $X_2$ is ethylene, propylene, butylene, pentylene, or hexylene; and preferably $X_2$ is butylene. Specifically, $R_1$ and $R_2$ are hydrogen, $A_1$ is carboxylic acid, $X_1$ is phenylene and $X_2$ is butylene.

Generally, the Formulae 1, 2 and 3 structural units of the terpolymer have specific ratios, for example, wherein the structural units corresponding to Formula 1 constitute at least about 80 wt. %, particularly at least about 85 wt. %, and more particularly at least about 90 wt. % or from about 80 wt. % to about 95 wt. %, from about 85 wt. % to about 95 wt. %, from about 85 wt. % to about 93 wt. % or from about 88 wt. % to about 92 wt. % based on the total weight of structural units of Formulae 1, 2, and 3 in the polymer, calculated based on the monomers of Formulae 11, 22, and 33 used in the polymerization reaction, and the weight ratio of the structural unit corresponding to Formula 2 to the structural unit corresponding to Formula 3 is from about 4:1 to about 1:4, or about 1:1.

Further, the ratio of structural units when expressed as the mole fraction of the structural unit of Formula 1 in the polymer is at least about 0.87 or from about 0.87 to about 0.94, or from about 0.9 to about 0.92 based on the total number of moles of the structural units of Formulae 1, 2, and 3, and the mole ratio of the structural unit of Formula 2 to the structural unit of Formula 3 is from about 0.2:1 to about 7:1, from about 0.2:1 to about 3.5:1; from about 0.5:1 to about 1.3:1, from about 0.8 to about 0.9, or about 0.85:1; again these calculations are performed using the amounts of monomers of Formulae 11, 22, and 33 used in the polymerization reaction. It is not necessary to calculate conversion.

In some aspects, the crosslinked cation exchange polymer comprises units corresponding to Formulae 1A, 2A, and 3A, wherein Formula 1A, Formula 2A and Formula 3A correspond to the following structures.

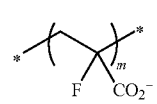

Formula 1A

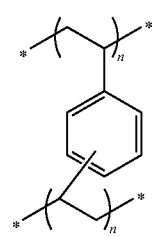

Formula 2A

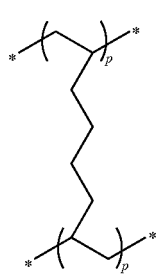

Formula 3A

In Formula 1 or 1A, the carboxylic acid can be in the acid form (i.e., balanced with hydrogen), in salt form (i.e., balanced with a counter-ion such as $Ca^{2+}$, $Mg^{2+}$, $Na^+$, $NH_4^+$, and the like) or in an ester form (i.e., balanced with an alkyl, such as methyl). Preferably, the carboxylic acid is in the salt form and balanced with a $Ca^{2+}$ counterion.

When the carboxylic acid of the crosslinked cation exchange form is balanced with a divalent counterion, two carboxylic acid groups can be associated with the one divalent cation.

The polymers described herein are generally random polymers wherein the exact order of the structural units of Formulae 1, 2, or 3 (derived from monomers of Formulae 11, 22, or 33), or 1A, 2A, or 3A (derived from monomers of Formulae 11A, 22A, or 33A) is not predetermined.

A cation exchange polymer derived from monomers of Formulae 11, 22, and 33, followed by hydrolysis, can have the structure as follows:

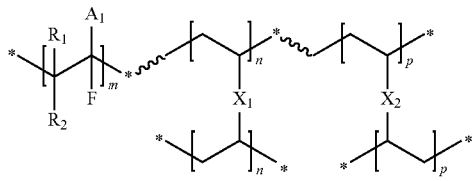

Formula 40 wherein $R_1$, $R_2$, $A_1$, $X_1$, and $X_2$ are as defined in connection with Formulae 1, 2, and 3 and m is in the range of from about 85 to about 93 mol %, n is in the range of from about 1 to about 10 mol % and p is in the range of from about 1 to about 10 mol % calculated based on the ratio of monomers and crosslinkers added to the polymerization mixture. The wavy bonds in the polymer structures of Formula 40 are included to represent the random attachment of structural units to one another wherein the structural unit of Formula 1 can be attached to another structural unit of Formula 1, a structural unit of Formula 2, or a structural unit of Formula 3; the structural units of Formulae 2 and 3 have the same range of attachment possibilities.

Using the polymerization process described herein, with monomers of Formulae 11A, 22A and 33A, followed by hydrolysis and calcium ion exchange, a polymer having the general structure shown below is obtained:

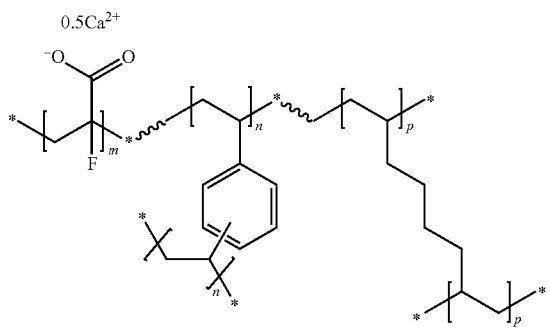

Formula 40A wherein m is in the range of from about 85 to about 93 mol %, n is in the range of from about 1 to about 10 mol % and p is in the range of from about 1 to about 10 mol %, calculated based on the ratios of monomers and crosslinkers added to the polymerization mixture. The wavy bonds in the polymer structures of Formula 40A are included to represent the random attachment of structural units to one another wherein the structural unit of Formula 1A can be attached to another structural unit of Formula 1A, a structural unit of Formula 2A, or a structural unit of Formula 3A; the structural units of Formulae 2A and 3A have the same range of attachment possibilities.

The crosslinked cation exchange polymer is generally a reaction product of a polymerization mixture that is subjected to polymerization conditions. The polymerization mixture may also contain components that are not chemically incorporated into the polymer. The crosslinked cation exchange polymer typically comprises a fluoro group and an acid group that is the product of the polymerization of three different monomer units where one monomer comprises a fluoro group and an acid group, another monomer is a difunctional arylene monomer and a third monomer is a difunctional alkylene, ether- or amide-containing monomer. More specifically, the crosslinked cation exchange polymer can be a reaction product of a polymerization mixture comprising monomers of Formulae 11, 22, 33. The monomer of Formula 11, the monomer of Formula 22, and the monomer of Formula 33 have the general formulas:

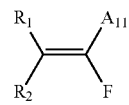

Formula 11

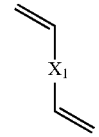

Formula 22

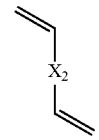

Formula 33 wherein $R_1$ and $R_2$ are as defined in connection with Formula 1, $X_1$ is as defined in connection with Formula 2, $X_2$ is as defined in connection with Formula 3, and $A_{11}$ is an optionally protected carboxylic, phosphonic, or phosphoric.

Preferably, $A_{11}$ is a protected carboxylic, phosphonic, or phosphoric.

The polymerization mixture typically further comprises a polymerization initiator.

The reaction product of the polymerization mixture comprising Formulae 11, 22, 33 comprises a polymer having protected acid groups and comprising units corresponding to Formula 10 and units corresponding to Formulae 2 and 3. Polymer products having protected acid groups can be hydrolyzed to form a polymer having unprotected acid groups and comprising units corresponding to Formulae 1, 2, and 3. The structural units corresponding to Formula 10 have the structure

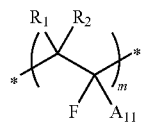

Formula 10 wherein $R_1$, $R_2$, and $A_{11}$ are as defined in connection with Formula 11 and m is as defined in connection with Formula 1.

In any of the methods of the invention wherein the crosslinked cation exchange polymer is a reaction product of a polymerization mixture of monomers, $A_{11}$ can be a protected carboxylic, phosphonic, or phosphoric. The polymer formed in the polymerization reaction contains protected carboxylic, phosphonic, or phosphoric groups. A hydrolysis agent can be added to the polymer formed in the polymerization reaction to hydrolyze these protected groups, converting them to carboxylic, phosphonic, or phosphoric groups, or other methods of deprotection well known in the art can be used. The hydrolyzed polymer is preferably subjected to ion exchange to obtain a preferred polymer salt for therapeutic use.

Generally, the polymerization reaction mixture comprises at least about 85 wt. % or from about 80 wt. % to about 95 wt. % of monomers corresponding to Formula 11 based on the total weight of the monomers corresponding to Formulae 11, 22, and 33; and the mixture having a weight ratio of the monomer corresponding to Formula 22 to the monomer corresponding to Formula 33 from about 4:1 to about 1:4, from about 2:1 to 1:2, or about 1:1.

The polymerization reaction mixture can comprise a unit corresponding to Formula 11 having a mole fraction of at least about 0.87 or from about 0.87 to about 0.94 based on the total number of moles of the monomers corresponding to Formulae 11, 22, and 33 and the mixture having a mole ratio of the monomer corresponding to Formula 22 to the monomer corresponding to Formula 33 of from about 0.2:1 to about 7:1, from about 0.2:1 to about 3.5:1; from about 0.5:1 to about 1.3:1, from about 0.8 to about 0.9, or about 0.85:1.

Particular crosslinked cation exchange polymers are the reaction product of a monomer corresponding to Formula 11A, a monomer corresponding to Formula 22A, a monomer corresponding to Formula 33A, and a polymerization initiator. The monomers corresponding to Formulae 11A, 22A, and 33A have the structure:

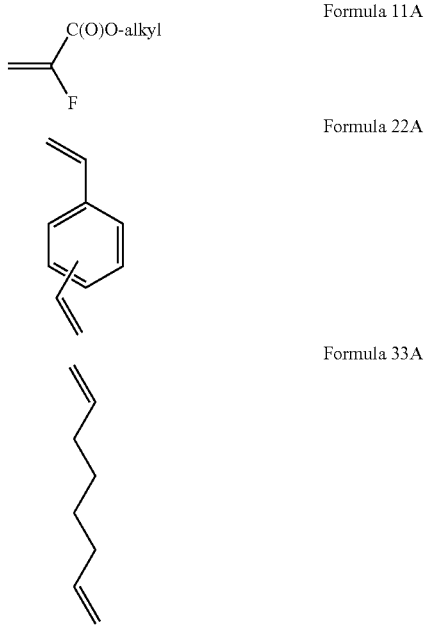

Formula 11A

Formula 22A

Formula 33A wherein alkyl is preferably selected from methyl, ethyl, propyl, iso-propyl, butyl, iso-butyl, sec-butyl, tert-butyl, pentyl, iso-pentyl, sec-pentyl, or tert-pentyl. Most preferably, the alkyl group is methyl or tert-butyl. The —O-alkyl moiety protects the carboxyl moiety from reacting with other reactive moieties during the polymerization reaction and can be removed by hydrolysis or other deprotection methods as described in more detail below.

Further, the reaction mixture contains at least about 80 wt. %, particularly at least about 85 wt. %, and more particularly at least about 90 wt. % or from about 80 wt. % to about 95 wt. %, from about 85 wt. % to about 95 wt. %, from about 85 wt. % to about 93 wt. % or from about 88 wt. % to about 92 wt. % of monomers corresponding to Formula 11A based on the total weight of monomers of Formulae 11A, 22A, and 33A and has a weight ratio of the monomer corresponding to Formula 22A to the monomer corresponding to Formula 33A of from about 4:1 to about 1:4 or about 1:1. Additionally, the reaction mixture can have a mole fraction of at least about 0.87 or from about 0.87 to about 0.94 of the monomer of Formula 11A based on the total number of moles of the monomers of Formulae 11A, 22A, and 33A and the mixture has a mole ratio of the monomer of Formula 22A to the monomer of Formula 33A of from about 0.2:1 to about 7:1, from about 0.2:1 to about 3.5:1; from about 0.5:1 to about 1.3:1, from about 0.8 to about 0.9, or about 0.85:1.

Generally, the reaction mixture contains from about 80 wt. % to about 95 wt. % of monomers corresponding to Formula 11A based on the total weight of monomers corresponding to Formulae 11A, 22A, and 33A. Additionally, the weight ratio of the monomer corresponding to Formula 22A to the monomer corresponding to Formula 33A of from about 4:1 to about 1:4 or about 1:1. Further, the reaction mixture can have a mole fraction of from about 0.9 to about 0.92 of the monomer of Formula 11A based on the total number of moles of the monomers of Formulae 11A, 22A, and 33A. Also, the mixture has a mole ratio of the monomer of Formula 22A to the monomer of Formula 33A of from about 0.2:1 to about 7:1, from about 0.2:1 to about 3.5:1; from about 0.5:1 to about 1.3:1, from about 0.8 to about 0.9, or about 0.85:1.

An initiated polymerization reaction is employed where a polymerization initiator is used in the polymerization reaction mixture to aid initiation of the polymerization reaction. When preparing poly(methylfluoro acrylate) or (polyMeFA) or any other crosslinked cation exchange polymer of the invention in a suspension polymerization reaction, the nature of the free radical initiator plays a role in the quality of the suspension in terms of polymer particle stability, yield of polymer particles, and the polymer particle shape. Use of water-insoluble free radical initiators, such as lauroyl peroxide, can produce polymer particles in a high yield. Without being bound by any particular theory, it is believed that a water-insoluble free radical initiator initiates polymerization primarily within the dispersed phase containing the monomers of Formulae 11, 22, and 33. Such a reaction scheme provides polymer particles rather than a bulk polymer gel. Thus, the process uses free radical initiators with water solubility lower than 0.1 g/L, particularly lower than 0.01 g/L. Polymethylfluoroacrylate particles can be produced with a combination of a low water solubility free radical initiator and the presence of a salt in the aqueous phase, such as sodium chloride.

The polymerization initiator can be chosen from a variety of classes of initiators. For instance, initiators that generate polymer initiating radicals upon exposure to heat include peroxides, persulfates or azo type initiators (e.g., 2,2'-azobis (2-methylpropionitrile), lauroyl peroxide (LPO), tert-butyl hydro peroxide, dimethyl-2,2'-azobis(2-methylpropionate), 2,2'-azobis[2-methyl-N-(2-hydroxyethyl)propionamide], 2,2'-azobis[2-(2-imidazolin-2-yl) propane], (2,2"-azo bis(2, 4-dimethylvaleronitrile), azobisisobutyronitrile (AIBN) or a combination thereof. Another class of polymer initiating radicals is radicals generated from redox reactions, such as persulfates and amines. Radicals can also be generated by exposing certain initiators to UV light or exposure to air.

For those polymerization reactions that contain additional components in the polymerization mixture that are not intended to be incorporated into the polymer, such additional components typically comprise surfactants, solvents, salts, buffers, aqueous phase polymerization inhibitors and/or other components known to those of skill in the art.

When the polymerization is carried out in a suspension mode, the additional components may be contained in an aqueous phase while the monomers and initiator may be contained in an organic phase. When an aqueous phase is present, the aqueous phase may be comprised of water, surfactants, stabilizers, buffers, salts, and polymerization inhibitors.

A surfactant may be selected from the group consisting of anionic, cationic, nonionic, amphoteric, zwitterionic, or a combination thereof. Anionic surfactants are typically based on sulfate, sulfonate or carboxylate anions. These surfactants include, sodium dodecyl sulfate (SDS), ammonium lauryl sulfate, other alkyl sulfate salts, sodium laureth sulfate (or sodium lauryl ether sulfate (SLES)), N-lauroylsarcosine sodium salt, lauryldimethylamine-oxide (LDAO), ethyltrimethylammoniumbromide (CTAB), bis(2-ethylhexyl)sulfosuccinate sodium salt, alkyl benzene sulfonate, soaps, fatty acid salts, or a combination thereof.

Cationic surfactants, for example, contain quaternary ammonium cations. These surfactants are cetyl trimethylammonium bromide (CTAB or hexadecyl trimethyl ammonium bromide), cetylpyridinium chloride (CPC), polyethoxylated tallow amine (POEA), benzalkonium chloride (BAC), benzethonium chloride (BZT), or a combination thereof.

Zwitterionic or amphoteric surfactants include dodecyl betaine, dodecyl dimethylamine oxide, cocamidopropyl betaine, coco ampho glycinate, or a combination thereof.

Nonionic surfactants include alkyl poly(ethylene oxide), copolymers of poly(ethylene oxide) and poly(propylene oxide) (commercially called Poloxamers or Poloxamines), alkyl polyglucosides (including octyl glucoside, decyl maltoside) fatty alcohols, cetyl alcohol, oleyl alcohol, cocamide MEA, cocamide DEA, or a combination thereof. Other pharmaceutically acceptable surfactants are well known in the art and are described in McCutcheon's Emulsifiers and Detergents, N. American Edition (2007).

Polymerization reaction stabilizers may be selected from the group consisting of organic polymers and inorganic particulate stabilizers. Examples include polyvinyl alcohol-co-vinylacetate and its range of hydrolyzed products, polyvinylacetate, polyvinylpyrolidinone, salts of polyacrylic acid, cellulose ethers, natural gums, or a combination thereof.

Buffers may be selected from the group consisting of, for example, 4-2-hydroxyethyl-1-piperazineethanesulfonic acid, 2-{[tris(hydroxymethyl)methyl]amino}ethanesulfonic acid, 3-(N-morpholino)propanesulfonic acid, piperazine-N,N'-bis(2-ethanesulfonic acid), sodium phosphate dibasic heptahydrate, sodium phosphate monobasic monohydrate or a combination thereof.

Polymerization reaction salts may be selected from the group consisting of potassium chloride, calcium chloride, potassium bromide, sodium bromide, sodium bicarbonate, ammonium peroxodisulfate, or a combination thereof.

Polymerization inhibitors may be used as known in the art and selected from the group consisting of 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1-aza-3,7-dioxabicyclo[3.3.0]octane-5-methanol, 2,2'-ethylidene-bis(4,6-di-tert-butylphenol), 2,2'-ethylidenebis(4,6-di-tert-butylphenyl) fluorophosphite, 2,2'-methylenebis(6-tert-butyl-4-ethylphenol), 2,2'-methylenebis(6-tert-butyl-4-methylphenol), 2,5-di-tert-butyl-4-methoxyphenol, 2,6-di-tert-butyl-4-(dimethylaminomethyl)phenol, 2-heptanone oxime, 3,3',5,5'-tetramethylbiphenyl-4,4'-diol, 3,9-bis(2,4-dicumylphenoxy)-2,4,8,10-tetraoxa-3,9-diphosphaspiro [5.5]undecane, 4,4-dimethyloxazolidine, 4-methyl-2-pentanone oxime, 5-ethyl-1-aza-3,7-dioxabicyclo[3.3.0]octane, 6,6'-dihydroxy-5,5'-dimethoxy-[1,1'-biphenyl]-3,3'-dicarboxaldehyde, distearyl-3,3'-thiodipropionate, ditetradecyl-3,3'-thiodipropionate, ditridecyl-3,3'-thiodipropionate, octadecyl-3-(3,5-di-tert-butyl-4-hydroxyphenyl)propionate, pentaerythritol tetrakis(3,5-di-tert-butyl-4-hydroxyhydrocinnamate), poly(1,2-dihydro-2,2,4-trimethylquinoline), sodium D-isoascorbate monohydrate, tetrakis(2,4-di-tert-butylphenyl)-4,4'-biphenyldiphosphonite, tris(3,5-di-tert-butyl-4-hydroxybenzyl) isocyanurate, tris(4-tert-butyl-3-hydroxy-2,6-dimethylbenzyl) isocyanurate, sodium nitrite or a combination thereof.

Generally, the polymerization mixture is subjected to polymerization conditions. While suspension polymerization is preferred, as already discussed herein, the polymers of this invention may also be prepared in bulk, solution or emulsion polymerization processes. The details of such processes are within the skill of one of ordinary skill in the art based on the disclosure of this invention. The polymerization conditions typically include polymerization reaction temperatures, pressures, mixing and reactor geometry, sequence and rate of addition of polymerization mixtures and the like.

Polymerization temperatures are typically in the range of from about 50 to 100° C. Polymerization pressures are typically run at atmospheric pressure, but can be run at higher pressures (for example 130 PSI of nitrogen). Polymerization depends on the scale of the polymerization and the equipment used, and is within the skill of one of ordinary skill in the art. Various alpha-fluoroacrylate polymers and the synthesis of these polymers are described in U.S. Patent Application Publication No. 2005/0220752, herein incorporated by reference.

As described in more detail in connection with the examples herein, the crosslinked cation exchange polymer can be synthesized in a polymerization suspension polymerization reaction by preparing an organic phase and an aqueous phase. The organic phase typically contains a monomer of Formula 11, a monomer of Formula 22, a monomer of Formula 33, and a polymerization initiator. The aqueous phase contains a suspension stabilizer, a water soluble salt, water, and optionally a buffer. The organic phase and the aqueous phase are then combined and stirred under nitrogen. The mixture is generally heated to about 60° C. to about 80° C. for about 2.5 to about 3.5 hours, allowed to rise up to 95° C. after polymerization is initiated, and then cooled to room temperature. After cooling, the aqueous phase is removed. Water is added to the mixture, the mixture is stirred, and the resulting solid is filtered. The solid is washed with water, alcohol or alcohol/water mixtures.

As described above, polymerization suspension stabilizers, such as polyvinyl alcohol, are used to prevent coalescence of particles during the polymerization process. Further, it has been observed that the addition of sodium chloride in the aqueous phase decreased coalescence and particle aggregation. Other suitable salts for this purpose include salts that are soluble in the aqueous phase. Water soluble salts are added at a concentration of from about 0.1 wt. % to about 10 wt. %, particularly from about 2 wt. % to about 5 wt. % and even more particularly from about 3 wt. % to about 4 wt. %.

Preferably, an organic phase of methyl 2-fluoroacrylate (90 wt. %), 1,7-octadiene (5 wt. %) and divinylbenzene (5 wt. %) is prepared and 0.5 wt. % of lauroyl peroxide is added to initiate the polymerization reaction. Additionally, an aqueous phase of water, polyvinyl alcohol, phosphates, sodium chloride, and sodium nitrite is prepared. Under nitrogen and while keeping the temperature below about 30° C., the aqueous and organic phases are mixed together. Once mixed completely, the reaction mixture is gradually heated with continuous stirring. After the polymerization reaction is initiated, the temperature of the reaction mixture is allowed to rise up to about 95° C. Once the polymerization reaction is complete, the reaction mixture is cooled to room temperature and the aqueous phase is removed. The solid can be isolated by filtration after water is added to the mixture. The resulting product is a crosslinked (methyl 2-fluoroacrylate)-divinylbenzene-1,7-octadiene terpolymer.

As discussed herein, after polymerization, the product may be hydrolyzed or otherwise deprotected by methods known in the art. For hydrolysis of the polymer having ester groups to form a polymer having carboxylic acid groups, preferably, the polymer is hydrolyzed with a strong base (e.g., NaOH, KOH, $Mg(OH)_2$, or $Ca(OH)_2$) to remove the alkyl (e.g., methyl) group and form the carboxylate salt. Depending on the pH of the hydrolysis mixture, the proton form of the (2-fluoroacrylic acid)-divinylbenzene-1,7-octadiene terpolymer is formed. Alternatively, the polymer can be hydrolyzed with a strong acid (e.g., HCl) to form the carboxylate salt. Preferably, the (methyl 2-fluoroacrylate)-divinylbenzene-1,7-octadiene terpolymer is hydrolyzed with an excess of aqueous sodium hydroxide solution at a temperature from about 30° C. to about 100° C. to yield (sodium 2-fluoroacrylate)-divinylbenzene-1,7-octadiene terpolymer. Typically, the hydrolysis reaction is carried out for about 15 to 25 hours. After hydrolysis, the solid is filtered and washed with water and/or an alcohol.

The cation of the polymer salt formed in the hydrolysis reaction or other deprotection step depends on the base used in that step. For example, when sodium hydroxide is used as the base, the sodium salt of the polymer is formed. This sodium ion can be exchanged for another cation by contacting the sodium salt with an excess of an aqueous metal salt to yield an insoluble solid of the desired polymer salt. After the desired ion exchange, the product is washed with an alcohol and/or water and dried directly or dried after a dewatering treatment with denatured alcohol; preferably, the product is washed with water and dried directly. For example, the sodium salt of the cation exchange polymer is converted to the calcium salt by washing with a solution that substitutes calcium for sodium, for example, by using calcium chloride, calcium acetate, calcium lactate gluconate, or a combination thereof. And, more specifically, to exchange sodium ions for calcium ions, the (sodium 2-fluoroacrylate)-divinylbenzene-1,7-octadiene terpolymer is contacted with an excess of aqueous calcium chloride to yield an insoluble solid of crosslinked (calcium 2-fluoroacrylate)-divinylbenzene-1,7-octadiene terpolymer. If the pH of the hydrolysis mixture is sufficiently low, the proton form of the (2-fluoroacrylic acid)-divinylbenzene-1,7-octadiene terpolymer is formed.

Using this suspension polymerization process, a crosslinked polyMeFA polymer is isolated in good yield, generally above about 85%, more specifically above about 90%, and even more specifically above about 93%. The yield of the second step (i.e., hydrolysis) preferably occurs in 100%, providing an overall yield after hydrolysis of above about 85%, more specifically above about 90%, and even more specifically above about 93%.

To add the linear polyol to the composition, the salt of the polymer is slurried with an aqueous solution of polyol (e.g., sorbitol), typically with the slurry containing an excess amount of polyol based on polymer weight. Performing this step can reduce inorganic fluoride in the composition. The slurry is maintained under conditions known to those of skill in the art, such as for at least 3 hours and ambient temperature and pressure. The solids are then filtered off and dried to desired moisture content.

The methods of treatment of hypertension, hyperkalemia, and chronic kidney disease can be used for a variety of treatment periods including treatment periods of 1, 2, 4, 6, 8, 12, 16, 20, 24, 28, 32, 36, 40, 44, 48, 52, or more weeks. The treatment period can also be 2 years, 3 years, 4 years, 5 years, or more.

When treating the patients for hyperkalemia or chronic kidney disease using the methods of the invention, the patient can have an estimated glomerular filtration rate (eGFR) from about 15 mL/min/1.73 $m^2$ to about 44 mL/min/1.73 $m^2$.

The methods of treating hyperkalemia, methods of treating hypertension in a patient having chronic kidney disease, type 2 diabetes, heart failure or a combination thereof, and methods of treating chronic kidney disease of the invention can cause several improvements such as a decrease in the patient's serum potassium level after 48 hours, or more of treatment as compared to the patient's serum potassium level before treatment with the potassium-binding agent; an increase in the patient's eGFR after 2, 3, 4, 5, 6, months or more of treatment as compared to the patient's eGFR before treatment with the potassium-binding agent; a decrease in the patient's urine albumin:creatinine ratio (ACR) after 2, 3, 4, 5, 6, months or more of treatment as compared to the patient's urine ACR before treatment with the potassium-binding agent; a decrease in the patient's systolic and diastolic blood pressure after 1, 2, 3, 4, 5, 6, 7 days or more of treatment as compared to the patient's systolic and diastolic blood pressure before treatment with the potassium-binding agent; a decrease in the patient's serum aldosterone level after 6, 12, 24, 48, 72, hours or more of treatment as compared to the patient's serum aldosterone level before treatment with the potassium-binding agent, or a combination thereof.

For the changes in serum potassium level, eGFR, blood pressure, and ACR, it is understood that the potassium-binding agent can be any one of the agents described herein even when the method is described relating to administration of 2-fluoroacrylate-divinylbenzene-1,7-octadiene copolymer crosslinked in the salt or acid form.

The methods of treating hyperkalemia in a chronic kidney disease patient in need thereof optionally being treated with an effective amount of a renin-angiotensin-aldosterone system (RAAS) agent comprise administering an effective amount of the potassium-binding agent to the patient and observing either (i) a decrease in the patient's serum creatinine level as compared to the patient's serum creatinine level before treatment with the potassium-binding agent, (ii) an increase in the time to progression of end stage renal disease as compared to a chronic kidney disease patient optionally treated with a RAAS agent but not treated with the potassium-binding agent, (iii) an increase in survival as compared to a chronic kidney disease patient optionally treated with a RAAS agent but not treated with the potassium-binding agent, or (iv) an increase or stabilization of estimated glomerular filtration rate (eGFR) as compared to the patient's eGFR before treatment with the potassium-binding agent, all indicating an increase or stabilization of the patient's kidney function.

The potassium-binding agent can be 2-fluoroacrylate-divinylbenzene-1,7-octadiene copolymer crosslinked in the salt or acid form.

The methods of treating hyperkalemia, methods of treating hypertension in a patient having chronic kidney disease, type 2 diabetes, heart failure or a combination thereof, and methods of treating chronic kidney disease can result in the patient's eGFR after treatment with the potassium-binding agent being increased by at least 4, 5, 6 mL/min/1.73 m$^2$ or more as compared to the patient's eGFR before treatment with the potassium-binding agent When treating hypertension, hyperkalemia, or chronic kidney disease in patients in need thereof, the effective amount of the potassium-binding agent comprises up to a maximum daily dose of 60 grams. The effective amount of the potassium-binding agent can be a daily dose of from about 3 grams to about 60 grams; from about 5 grams to about 60 grams; from about 7 grams to about 60 grams; from about 10 grams to about 60 grams; from about 12 grams to about 60 grams; or from about 15 grams to about 60 grams.

The effective amount of the potassium-binding agent can be a daily dose of from about 3 grams to about 40 grams; from about 5 grams to about 40 grams; from about 10 grams to about 40 grams; or from about 15 grams to about 40 grams.

Particularly, the effective amount of the potassium-binding agent can be a daily dose of about 18 gram to about 60 grams or about 18 grams to about 40 grams.

When the potassium binding agent is 2-fluoroacrylate-divinylbenzene-1,7-octadiene copolymer crosslinked in the salt form, the dose in grams is calculated by determining the amount of the salt form of crosslinked 2-fluoroacrylate-divinylbenzene-1,7-octadiene copolymer plus the calcium counterion. So, this dose does not include the water and sorbitol that may be contained in the powder that is administered to the patient Dosing can be once a day, twice a day or three times per day, however, once a day or twice a day is preferred, with once a day being most preferred.

The methods of treating hypertension, hyperkalemia, or chronic kidney disease of the invention can further comprise administering an effective amount of a renin-angiotensin-aldosterone system (RAAS) agent to the patient; determining the serum potassium level in the patient; and increasing the amount of the potassium-binding agent subsequently administered to the patient based on the serum potassium level if greater than or equal to 5.1 mEq/L. The methods of hypertension, hyperkalemia, or chronic kidney disease can further comprise a step wherein the amount of the potassium-binding agent was increased by 5 g or 10 g per day.

The methods of treating hypertension, hyperkalemia, or chronic kidney disease of the invention can further comprise administering an effective amount of a renin-angiotensin-aldosterone system (RAAS) agent to the patient; determining the serum potassium level in the patient; decreasing the amount of the potassium-binding agent subsequently administered to the patient based on the serum potassium level if less than 4.0 mEq/L. The method of treating hypertension, hyperkalemia, or chronic kidney disease can further comprise a step wherein the amount of the potassium-binding agent was decreased by 5 g or 10 g per day.

The methods hypertension, hyperkalemia, or chronic kidney disease of the invention can further comprise treating proteinuria.

Further, the methods of treating hypertension, hyperkalemia, proteinuria, or chronic kidney disease may include treating the patient with an effective amount of a RAAS agent, the RAAS agent being an angiotensin converting enzyme (ACE) inhibitor, an angiotensin receptor blocker (ARB), an aldosterone antagonist (AA), an aldosterone synthase inhibitor, or a combination thereof. Particularly, the patient may be treated with an effective amount of a RAAS agent, the RAAS agent is an ACE inhibitor, an ARB, or a combination thereof.

For the methods where the patient is being treated with an effective amount of a RAAS agent, the effective amount of the RAAS agent comprises up to a maximum daily tolerated dose.

The RAAS agent comprises fosinopril, ramipril, captopril, lisinopril, trandolapril, moexipril, quinapril, enalapril, benazepril, perindopril, eprosartan, olmesartan, losartan, telmisartan, valsartan, candesartan, irbesartan, azilsartan medoxomil, spironolactone, eplerenone, or a combination thereof.

The maximum daily tolerated dose of specific RAAS agents is 4 mg/day (trandolapril), 8 mg/day (perindopril), 20 mg/day (ramipril), 30 mg/day (moexipril), 32 mg/day (candesartan), 40 mg/day (fosinopril, lisinopril, enalapril, benazepril, olmesartan), 80 mg/day (quinapril telmisartan, azilsartan, medoxomil), 100 mg/day (losartan), 300 mg/day (captopril, irbesartan), 320 mg/day (valsartan), or 800 mg/day (eprosartan).

When the RAAS agent comprises spironolactone, the maximum daily tolerated dose is 200 mg/day.

When the RAAS agent comprises eplerenone, the maximum daily tolerated dose is 50 mg/day.

Patients being treated with the methods of treating hypertension, hyperkalemia or chronic kidney disease of the invention can further be treated with an effective amount of a beta-adrenergic blocking agent. The beta-adrenergic blocking agent can comprise betaxolol, bisoprolol, atenolol, metoprolol, nebivolol, metoprolol, esmolol, acebutolol, propranolol, nadolol, carvedilol, labetalol, sotalol, timolol, carteolol, penbutolol, pindolol, or a combination thereof.

In all of the methods described above, the potassium-binding agent can be 2-fluoroacrylate-divinylbenzene-1,7-octadiene copolymer crosslinked in the salt or acid form.

The term "treating" as used herein includes achieving a therapeutic benefit. By therapeutic benefit is meant eradication, amelioration, or prevention of the underlying disorder being treated. For example, in a hyperkalemia patient, therapeutic benefit includes eradication or amelioration of the underlying hyperkalemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of a potassium-binding polymer to a patient experiencing hyperkalemia provides therapeutic benefit not only when the patient's serum potassium level is decreased, but also when an improvement is observed in the patient with respect to other disorders that accompany hyperkalemia, like renal failure. In some treatment regimens, the crosslinked cation exchange polymer or composition of the invention may be administered to a patient at risk of developing hyperkalemia or to a patient reporting one or more of the physiological symptoms of hyperkalemia, even though a diagnosis of hyperkalemia may not have been made.

End stage renal disease is characterized by a patient being on dialysis or having a renal transplant.

Proteinuria, also known as albuminuria or urine albuminis, is a condition in which urine contains an abnormal amount of protein. Albumin is the main protein in the blood. Proteins are the building blocks for all body parts, including muscles, bones, hair, and nails. Proteins in the blood also perform a number of important functions. They protect the body from infection, help blood clot, and keep the right amount of fluid circulating throughout the body.

As blood passes through healthy kidneys, they filter out the waste products and leave in the things the body needs, like albumin and other proteins. Most proteins are too big to pass through the kidneys' filters into the urine. However, proteins from the blood can leak into the urine when the filters of the kidney, called glomeruli, are damaged.

Proteinuria is a sign of chronic kidney disease (CKD), which can result from diabetes, high blood pressure, and diseases that cause inflammation in the kidneys. For this reason, testing for albumin in the urine is part of a routine medical assessment for everyone. Kidney disease is sometimes called renal disease. If CKD progresses, it can lead to end-stage renal disease (ESRD), when the kidneys fail completely. A person with ESRD must receive a kidney transplant or regular blood-cleansing treatments called dialysis.

The potassium-binding polymers used in the methods of the invention can be administered as pharmaceutical compositions containing an effective amount, i.e., in an amount effective to achieve therapeutic or prophylactic benefit of the potassium-binding polymer and a pharmaceutically acceptable carrier. The actual amount effective for a particular application will depend on the patient (e.g., age, weight, etc.), the condition being treated, and the route of administration. Determination of an effective amount is well within the capabilities of those skilled in the art, especially in light of the disclosure herein. The effective amount for use in humans can be determined from animal models. For example, a dose for humans can be formulated to achieve gastrointestinal concentrations that have been found to be effective in animals.

The polymers and compositions described herein can be used as food products and/or food additives. They can be added to foods prior to consumption or while packaging.

The polymers or pharmaceutically acceptable salts thereof, or compositions described herein, can be delivered to the patient using a wide variety of routes or modes of administration. The most preferred routes for administration are oral, intestinal, or rectal. Rectal routes of administration are known to those of skill in the art. Intestinal routes of administration generally refer to administration directly into a segment of the gastrointestinal tract, e.g., through a gastrointestinal tube or through a stoma. The most preferred route for administration is oral.

The polymers (or pharmaceutically acceptable salts thereof) may be administered per se or in the form of a pharmaceutical composition wherein the active compound(s) is in admixture or mixture with one or more pharmaceutically acceptable excipient. Pharmaceutical compositions for use in accordance with the present invention may be formulated in conventional manner using one or more pharmaceutically acceptable excipients comprising carriers, diluents, and auxiliaries which facilitate processing of the active compounds into preparations which can be used physiologically. Proper composition is dependent upon the route of administration chosen.

For oral administration, the polymers or compositions of the invention can be formulated readily by combining the polymer or composition with pharmaceutically acceptable excipients well known in the art. Such excipients enable the compositions of the invention to be formulated as tablets, pills, dragees, capsules, liquids, gels, syrups, slurries, suspensions, wafers, and the like, for oral ingestion by a patient to be treated.

The oral composition can not have an enteric coating.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose or sucrose; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

The active ingredient (e.g., polymer) can constitute over about 20%, more particularly over about 40%, even more particularly over about 50%, and most particularly more than about 60% by weight of the oral dosage form, the remainder comprising suitable excipient(s). In compositions containing water and linear polyol, the polymer preferably constitutes over about 20%, more particularly over about 40%, and even more particularly over about 50% by weight of the oral dosage form.

The polymers of the invention can be provided as pharmaceutical compositions in the form of liquid compositions. The pharmaceutical composition can contain a polymer dispersed in a suitable liquid excipient. Suitable liquid excipients are known in the art; see, e.g., Remington's Pharmaceutical Sciences.

Unless otherwise indicated, an alkyl group as described herein alone or as part of another group is an optionally substituted linear saturated monovalent hydrocarbon radical containing from one to twenty carbon atoms and preferably one to eight carbon atoms, or an optionally substituted branched saturated monovalent hydrocarbon radical containing three to twenty carbon atoms, and preferably three to eight carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "amide moiety" as used herein represents a bivalent (i.e., difunctional) group including at least one amido linkage (i.e., 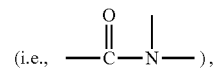 ), such as —C(O)—NR$_A$—R$_C$—NR$_B$—C(O)— wherein R$_A$ and R$_B$ are independently hydrogen or alkyl and R$_C$ is alkylene. For example, an amide moiety can be —C(O)—NH—(CH$_2$)$_p$—NH—C(O)— wherein p is an integer of 1 to 8.

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The terms "carboxylic acid group", "carboxylic" or "carboxyl" denote the monovalent radical —C(O)OH. Depending upon the pH conditions, the monovalent radical can be in the form —C(O)O$^-$ Q$^+$ wherein Q$^+$ is a cation (e.g., sodium), or two of the monovalent radicals in close proximity can bond with a divalent cation Q$^{2+}$ (e.g., calcium, magnesium), or a combination of these monovalent radicals and —C(O)OH are present.

The term "cycloalkyl" as used herein denotes optionally an optionally substituted cyclic saturated monovalent bridged or non-bridged hydrocarbon radical containing from three to eight carbon atoms in one ring and up to 20 carbon atoms in a multiple ring group. Exemplary unsubstituted cycloalkyl groups include cyclopropyl, cyclobutyl, cyclopentyl, cyclohexyl, cycloheptyl, cyclooctyl, adamantyl, norbornyl, and the like.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as methylene (—CH$_2$—) or ethylene (—CH$_2$CH$_2$—), and arylene denotes a bivalent aryl group such as o-phenylene, m-phenylene, or p-phenylene.

The term "ether moiety" as used herein represents a bivalent (i.e., difunctional) group including at least one ether linkage (i.e., —O—). For example, in Formulae 3 or 33 as defined herein, the ether moiety can be —R$_A$OR$_B$— or —R$_A$OR$_C$OR$_B$— wherein R$_A$, R$_B$ and R$_C$ are independently alkylene.

The term "heteroaryl," as used herein alone or as part of another group, denotes an optionally substituted monovalent monocyclic or bicyclic aromatic radical of 5 to 10 ring atoms, where one or more, preferably one, two, or three, ring atoms are heteroatoms independently selected from N, O, and S, and the remaining ring atoms are carbon. Exemplary heteroaryl moieties include benzofuranyl, benzo[d]thiazolyl, isoquinolinyl, quinolinyl, thiophenyl, imidazolyl, oxazolyl, quinolinyl, furanyl, thazolyl, pyridinyl, furyl, thienyl, pyridyl, oxazolyl, pyrrolyl, indolyl, quinolinyl, isoquinolinyl, and the like.

The term "heterocyclo," as used herein alone or as part of another group, denotes a saturated or unsaturated monovalent monocyclic group of 4 to 8 ring atoms, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, piperidino, morpholino, piperazino, and the like.

The term "hydrocarbon" as used herein describes a compound or radical consisting exclusively of the elements carbon and hydrogen.

The term "phosphonic" or "phosphonyl" denotes the monovalent radical

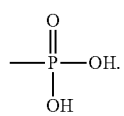

The term "phosphoric" or "phosphoryl" denotes the monovalent radical

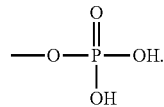

The term "protected" as used herein as part of another group denotes a group that blocks reaction at the protected portion of a compound while being easily removed under conditions that are sufficiently mild so as not to disturb other substituents of the compound. For example, a protected carboxylic acid group —C(O)OP$_g$ or a protected phosphoric acid group —OP(O)(OH)OP$_g$ or a protected phosphonic acid group —P(O)(OH)OP$_g$ each have a protecting group P$_g$ associated with the oxygen of the acid group wherein P$_g$ can be alkyl (e.g., methyl, ethyl, n-propyl, i-propyl, n-butyl, i-butyl, s-butyl, t-butyl, n-pentyl, i-pentyl, s-pentyl, t-pentyl, and the like), benzyl, silyl (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999. When the term "protected" introduces a list of possible protected groups, it is intended that the term apply to every member of that group. That is, the phrase "protected carboxylic, phosphonic or phosphoric" is to be interpreted as "protected carboxylic, protected phosphonic or protected phosphoric." Likewise, the phrase "optionally protected carboxylic, phosphoric or phosphonic" is to be interpreted as "optionally protected carboxylic, optionally protected phosphonic or optionally protected phosphoric."

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON(R$_A$)(R$_B$), wherein R$_A$ and R$_B$ are independently hydrogen, alkyl, or aryl), amino(—N(R$_A$)(R$_B$), wherein R$_A$ and R$_B$ are independently hydrogen, alkyl, or aryl), halo (fluoro, chloro, bromo, or iodo), silyl, nitro (—NO$_2$), an ether (—OR$_A$ wherein R$_A$ is alkyl or aryl), an ester (—OC(O)R$_A$ wherein R$_A$ is alkyl or aryl), keto (—C(O)R$_A$ wherein R$_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

Having described the invention in detail, it will be apparent that modifications and variations are possible without departing from the scope of the invention defined in the appended claims.

EXAMPLES

The following non-limiting examples are provided to further illustrate the present invention.

Example 1: Sorbitol-Loaded, Crosslinked (Calcium 2-Fluoroacrylate)-Divinylbenzene-1,7-Octadiene Copolymer Methyl 2-fluoroacrylate (MeFA) was purchased and was vacuum distilled before use. Divinylbenzene (DVB) was purchased from Aldrich, technical grade, 80%, mixture of isomers, and was used as received. 1,7-octadiene (ODE), lauroyl peroxide (LPO), polyvinyl alcohol (PVA) (typical molecular weight 85,000-146,000, 87-89% hydrolyzed), sodium chloride (NaCl), sodium phosphate dibasic heptahydrate ($Na_2HPO_4 \cdot 7H_2O$) and sodium phosphate monobasic monohydrate ($NaH_2PO_4 \cdot H_2O$) were purchased from commercial sources and used as received.

In an appropriately sized reactor with appropriate stirring and other equipment, a 90:5:5 weight ratio mixture of organic phase of monomers was prepared by mixing methyl 2-fluoroacrylate, 1,7-octadiene, and divinylbenzene. One-half part of lauroyl peroxide was added as an initiator of the polymerization reaction. A stabilizing aqueous phase was prepared from water, polyvinyl alcohol, phosphates, sodium chloride, and sodium nitrite. The aqueous and monomer phases were mixed together under nitrogen at atmospheric pressure, while maintaining the temperature below 30° C. The reaction mixture was gradually heated while stirring continuously. Once the polymerization reaction has started, the temperature of the reaction mixture was allowed to rise to a maximum of 95° C.

After completion of the polymerization reaction, the reaction mixture was cooled and the aqueous phase was removed. Water was added, the mixture was stirred, and the solid material was isolated by filtration. The solid was then washed with water to yield a crosslinked (methyl 2-fluoroacrylate)-divinylbenzene-1,7-octadiene copolymer. The (methyl 2-fluoroacrylate)-divinylbenzene-1,7-octadiene copolymer was hydrolyzed with an excess of aqueous sodium hydroxide solution at 90° C. for 24 hours to yield (sodium 2-fluoroacrylate)-divinylbenzene-1,7-octadiene copolymer. After hydrolysis, the solid was filtered and washed with water. The (sodium 2-fluoroacrylate)-divinylbenzene-1,7-octadiene copolymer was exposed at room temperature to an excess of aqueous calcium chloride solution to yield insoluble cross-linked (calcium 2-fluoroacrylate)-divinylbenzene-1,7-octadiene copolymer.

After the calcium ion exchange, the wet polymer is slurried with 25-30% w/w aqueous solution of sorbitol at ambient temperature to yield sorbitol-loaded polymer. Excess sorbitol was removed by filtration. The resulting polymer was dried at 20-30° C. until the desired moisture content (10-25 w/w/%) was reached. This provided a sorbitol-loaded, crosslinked (calcium 2-fluoroacrylate)-divinylbenzene-1,7-octadiene copolymer (5016CaS).

Example 2: Phase II Clinical Study

Study Design Overview. The study has two 5016CaS treatment periods: a treatment initiation period for 8 weeks, followed by a long-term maintenance period for an additional 44 weeks which allows treatment with 5016CaS for up to a total of one year (i.e., 52 weeks). Eligible non-hyperkalemic patients start a run-in period of 1 to 4 weeks in duration (Cohorts 1 and 2). Eligible hyperkalemic patients start treatment with 5016CaS immediately (Cohort 3). At the first occurrence of serum potassium ($K^+$)>5.0–<6.0 mEq/L, eligible patients from all three cohorts are assigned to one of two strata according to baseline serum potassium and received 5016CaS treatment at randomly assigned starting doses ranging from 10 to 40 g/day. The dose amount is based on the amount of the polymer anion plus calcium (e.g., on a water and sorbitol free basis). A 10 g dose of polymer anion plus calcium is equivalent to an 8.4 g dose of the polymer anion. The study duration is up to 62 weeks per patient (including screening and follow-up procedures) and the study population is approximately 306 patients. The study variables included change in serum potassium, blood pressure, estimated GFR and ACR.

Eligible patients are assigned to one of two 5016CaS treatment strata wherein Stratum 1 includes patients with serum $K^+$>5.0–5.5 mEq/L, these patients are randomized in a 1:1:1 ratio to receive either 10 g/day, 20 g/day, or 30 g/day 5016CaS starting doses within each study cohort. Stratum 2 includes patients with serum $K^+$>5.5–<6.0 mEq/L, these patients are randomized in a 1:1:1 ratio to receive 20 g/day, 30 g/day, or 40 g/day 5016CaS starting doses within each study cohort.

Patients start 5016CaS treatment at their assigned dose level on the evening of day 1. They continue taking losartan 100 mg/d (with or without spironolactone 25-50 mg/d) or pre-study ACEI and/or ARB with spironolactone 25-50 mg/d, (as per their Cohort 1 or 2 assignment), as well as any other protocol-allowed antihypertensive therapy. Patients in Cohort 3 continue their pre-study ACEI and/or ARB.

Dose and Route of 5016CaS Administration. 5016CaS was taken orally twice daily in equally divided doses for up to 52 weeks starting on day 1 (the evening dose only). Patients take 5016CaS twice a day with their regular meals (breakfast and dinner). The 5016CaS dose is adjusted as needed according to the appropriate titration algorithm (treatment initiation or long-term maintenance) starting on day 3 and up to the week 51 visit. The minimum allowed dose is 0 g/d (no 5016CaS dispensed) and the maximum dose is 60 g/d.

FIGS. 1-5 look at potassium reduction, blood pressure control, eGFR change and protein urea change by the following patient subtypes: (1) patients with any amount of protein in the urine (2) patients with microalbuminuria (3) patients with macroalbuminuria and (4) patients with stage 4 chronic kidney disease (CKD). FIG. 1 shows that a serum potassium reduction was experienced by all of these patient types. FIGS. 2 and 3 showed blood pressure reductions and that 5016CaS was as effective in reducing blood pressure in all of the patient types. FIG. 4 shows that there was no significant increase in protein urea levels in any of the patient types, so 5016CaS effectively stabilized the patient's protein excretion. FIG. 5 shows that renal function appeared to stabilize in all patient types with a potential for improvement in renal function in patients with stage 4 CKD.

The study protocol was completed by 182 patients for the analysis following in this Example 2. A statistically significant number of these patients had an albumin creatinine ratio (ACR) of ≥30 mg/g and others had an ACR of >300 mg/g and an estimated glomerular filtration rate (eGFR) of 15 to 44 mL/min/1.73 $m^2$ at baseline. For all of these patients, the patient's serum potassium concentration decreased from an average of 5.27 mEq/L at baseline to an average of 4.57 mEq/L at 24 weeks. For patients having an ACR≥30 mg/g, the patient's serum potassium concentration decreased from an average of 5.28 mEq/L at baseline to an average of 4.60 mEq/L at 24 weeks. For patients having an ACR>300 mg/g, the patient's serum potassium concentration decreased from an average of 5.35 mEq/L at baseline to an average of 4.65 mEq/L at 24 weeks. For patients having an eGFR of 15 to 44 mL/min/1.73 $m^2$, the patient's serum potassium concentration decreased from an average of 5.33 mEq/L at baseline to an average of 4.59 mEq/L at 24 weeks.

For patients having an eGFR of 15 to 44 mL/min/1.73 $m^2$, the patient's eGFR increased from an average of 32 mL/min/1.73 $m^2$ at baseline to an average of 38 mL/min/1.73 $m^2$ at 24 weeks. This increase in eGFR for these patients was statistically significant.

For the patients in all groups and each group separately (e.g., ACR of ≥30 mg/g, ACR of >300 mg/g, eGFR of 15 to 44 mL/min/1.73 m$^2$), the ACR did not significantly change over the 24 week treatment period.

For all of these patients, the patient's systolic blood pressure decreased from an average of 154 at baseline to an average of 137 at 24 weeks and the patient's diastolic blood pressure decreased from an average of 83 at baseline to an average of 74 at 24 weeks. For patients having an ACR≥30 mg/g, the patient's systolic blood pressure decreased from an average of 154 at baseline to an average of 138 at 24 weeks and the patient's diastolic blood pressure decreased from an average of 84 at baseline to an average of 74 at 24 weeks. For patients having an ACR>300 mg/g, the patient's systolic blood pressure decreased from an average of 154 at baseline to an average of 137 at 24 weeks and the patient's diastolic blood pressure decreased from an average of 86 at baseline to an average of 73 at 24 weeks. For patients having an eGFR of 15 to 44 mL/min/1.73 m$^2$, the patient's systolic blood pressure decreased from an average of 152 at baseline to an average of 135 at 24 weeks and the patient's diastolic blood pressure decreased from an average of 82 at baseline to an average of 73 at 24 weeks.

FIGS. 6-9 present one year data from a certain cohort of 90 patients with pre-existing hyperkalemia that were taking a stable dose of a RAAS inhibitor that came into the trial without a run-in period. These figures show that kidney function (FIG. 6) and urinary protein excretion (FIG. 8) appeared to stabilize, with reductions in serum potassium (FIG. 7) and blood pressure (FIG. 9). When analyzing the twelve month data for these patients, the average eGFR was 46 mL/min/1.73 m$^2$ at baseline (BL), 49 mL/min/1.73 m$^2$ at one month (M1), 51 mL/min/1.73 m$^2$ at two months (M2), 49 mL/min/1.73 m$^2$ at six months (M6) and 48 mL/min/1.73 m$^2$ at twelve months (M12) (FIG. 6). The eGFR for these patients did not significantly change over the twelve month treatment period. These patients also experienced a significant decrease in serum potassium level. (FIG. 7) For example, the average serum potassium level was 5.3 mEq/L at baseline (BL), 4.5 mEq/L at one month (M1), 4.5 mEq/L at two months (M2), 4.6 mEq/L at six months (M6), and 4.6 mEq/L at twelve months (M12). These patients also had an average urine ACR of 853 mg/g at baseline (BL), 900 mg/g at one month (M1), 971 mg/g at two months (M2), 930 mg/g at six months (M6), and 802 mg/g at twelve months (M12). The average systolic blood pressure of these patients was 157 mmHg at baseline (BL), 138 mmHg at one month (M1), 139 mmHg at two months (M2), 138 mmHg at six months (M6), and 134 mmHg at twelve months (M12). The average diastolic blood pressure was 85 mmHg at baseline (BL), 74 mmHg at one month (M1), 73 mmHg at two months (M2), 73 mmHg at six months (M6), and 77 mmHg at twelve months (M12).

The mean change in serum potassium from baseline to week 4 or first dose titration, whichever comes first, is presented by stratum in Table 1. To be consistent with the study protocol, the most recent non-missing measurement of serum potassium was used for patients who did not titrate before the week 4 visit (last observation carried forward, i.e., LOCF). 5016CaS lowered serum potassium in all dose groups in both strata; the p-values indicate that the reduction is statistically significantly different from zero. The reference groups in both strata are the randomized starting doses chosen for the Phase III study.

TABLE 1

Estimated mean change from baseline in central serum K$^+$ to week 4 or first dose titration, by randomized starting dose within stratum

| At week 4 or prior to first titration | Stratum 1 Local serum K$^+$ >5.0-5.5 mEq/L | | | | Stratum 2 Local serum K$^+$ >5.5-<6.0 mEq/L | | | |
|---|---|---|---|---|---|---|---|---|
| | 10 g/d N = 74 | 20 g/d N = 73 | 30 g/d N = 73 | Overall N = 220 | 20 g/d N = 26 | 30 g/d N = 28 | 40 g/d N = 30 | Overall N = 84 |
| Change in serum K$^+$ (mEq/L) from baseline | | | | | | | | |
| n[a] | 73 | 73 | 72 | 218 | 26 | 27 | 30 | 83 |
| Least square mean ± standard error | −0.35 ± 0.066 | −0.51 ± 0.066 | −0.54 ± 0.066 | −0.47 ± 0.038 | −0.85 ± 0.136 | −0.95 ± 0.132 | −0.90 ± 0.127 | −0.90 ± 0.076 |
| 95% confidence interval | −0.48, −0.22 | −0.64, −0.38 | −0.67, −0.41 | −0.54, −0.39 | −1.12, −0.58 | −1.21, −0.68 | −1.15, −0.65 | −1.05, −0.75 |
| p-value[b] | <0.001 | <0.001 | <0.001 | <0.001 | <0.001 | <0.001 | <0.001 | <0.001 |
| Comparison to reference | | | | | | | | |
| Mean difference | reference | 0.17 | 0.19 | | reference | 0.097 | 0.050 | |
| 95% confidence interval | | −0.018, 0.35 | 0.006, 0.37 | | | −0.28, 0.48 | −0.32, 0.42 | |
| p-value[c] | | 0.076 | 0.043 | | | 0.61 | 0.79 | |

Column header counts include all randomized patients who received RLY5016 (intent-to-treat population) by each randomized starting dose within stratum. Each stratum is analyzed separately using a parallel lines analysis of covariance (ANCOVA) model where the outcome is change in semm K$^+$ from baseline. Each model contains a fixedeffect for randomized starting dose, cohort, and continuous baseline serum K$^+$. Estimates and confidence intervals for each randomized starting dose gives were generated using linear contrasts across the observed values of the covariates.
[a]Number of patients in the intent-to-treat population with non-missing baseline serum K$^+$ at baseline.
[b]p-values test the hypothesis that the mean change in semm K$^+$ from baseline is 0.
[c]p-values test the pairwise difference in change in serum K$^+$ from baseline between dose groups. Positive values indicate lager reduction from baseline as compared to the reference group.

5016CaS lowered serum potassium in all dose groups in both strata regardless of dose titration beginning as early as Day 3 and stabilizing after approximately Week 2. Most patients were able to maintain serum potassium before and after dose titration in the range of 4.0 mEq/L to 5.0 mEq/L in all dose groups in both strata.

The primary outcome, mean change from baseline in serum K (mEq/L) at week 4 or first 5016CaS dose titration analyzed using a parallel lines ANCOVA model, was −0.47±0.038 (p<0.001) in S1 and −0.90±0.076 (p<0.001) in S2. Mean K reduction after a median 2 days of treatment was −0.29±0.03 (S1) and −0.55±0.05 mEq/L (S2). Table 2 summarizes the means and changes from baseline, allowing titration.

TABLE 2

| | Stratum 1 ((S1), BL K >5.0-5.5 mEq/L) | | | Stratum 2 ((S2), BL K >5.5-<6.0 mEq/L) | | |
|---|---|---|---|---|---|---|
| | Baseline (n = 217) | Week 4 (n = 197) | Week 8 (n = 185) | Baseline (N = 84) | Week 4 (n = 70) | Week 8 (n = 70) |
| Mean K (SE) (mEq/L) | 5.15 (0.02) | 4.54 (0.03) | 4.59 (0.03) | 5.64 (0.04) | 4.65 (0.06) | 4.52 (0.06) |
| LS Mean change (SE) (mEq/L) | — | −0.61 (0.03) | −0.55 (0.03) | — | −0.97 (0.06) | −1.10 (0.06) |

5016CaS reduced serum K within days of treatment initiation, an effect sustained over twelve months without significant adverse effects.

Example 3: Analysis of Systolic Blood Pressure from Phase II Clinical Study

The following section contains results of the repeated measures analyses of mean systolic blood pressure during the 8-week treatment initiation period of the Phase II Clinical Study disclosed in Example 2. Table 3 through Table 6 present the analyses of mean change from baseline. Tables 3 and 4 present the results for all patients; Tables 5 and 6 present subsets of the analyses according to hyperkalemia status at screening (Cohort 3). In general, patients in Stratum 2 (patients with serum $K^+$>5.5-<6.0 mEq/L) experience smaller mean decreases in blood pressure than patients in Stratum 1 (patients with serum $K^+$>5.0-5.5 mEq/L). Patients in Cohort 3, who entered the study hyperkalemic and did not participate in the run-in phase, contributed to the reduction in mean systolic blood pressure (Tables 5 and 6).

For Tables 3-6, column header counts include all randomized patients who received RLY5016 (intent-to-treat population) by each randomized starting dose within stratum. The data were derived from a mixed model for repeated measures where the outcome variable was a change in systolic blood pressure (SBP) from baseline. Each stratum was analyzed separately. Each model contained a fixed effect for cohort, randomized starting dose, time (visit), continuous baseline SBP, and randomized starting dose by visit interaction. The within-patient correlation was modeled using heterogeneous Toeplitz structure. Estimates, standard errors (SE), and confidence intervals for each randomized starting dose were generated using linear contrasts across the observed values of the covariates. Overall estimates, standard errors, and confidence intervals across randomized dosing groups assume equal distribution across dosing groups. The total patients in the analysis, N, were determined by the number of randomized patients who received RLY5016, had a baseline measure, and contributed at least one post-baseline measure to this analysis. Not all patients contributed measures at each visit.

TABLE 3

Estimated mean change from baseline in systolic blood pressure by randomized starting dose, all patients Stratum 1

| | Stratum 1—Local serum K+ >5.0-5.5 mEq/L | | | |
|---|---|---|---|---|
| Change in SBP from baseline (mmHg) | 10 g/d N = 74 | 20 g/d N = 73 | 30 g/d N = 73 | Overall N = 220 |
| Patients in analysis, N | 74 | 73 | 73 | 220 |
| Day 3, n | 70 | 70 | 72 | 212 |
| Least squares mean ± SE | −9.3 ± 1.8 | −4.9 ± 1.8 | −10.3 ± 1.8 | −8.2 ± 1.0 |
| 95% confidence interval | −12.8, −5.7 | −8.5, −1.4 | −13.9, −6.8 | −10.2, −6.1 |
| Week 1, n | 72 | 71 | 72 | 215 |
| Least squares mean ± SE | −11.1 ± 1.9 | −8.8 ± 2.0 | −12.0 ± 1.9 | −10.6 ± 1.1 |
| 95% confidence interval | −14.9, −7.3 | −12.6, −4.9 | −15.8, −8.2 | −12.8, −8.4 |
| Week 2, n | 70 | 70 | 71 | 211 |
| Least squares mean ± SE | −12.4 ± 2.0 | −5.7 ± 2.0 | −13.8 ± 2.0 | −10.6 ± 1.1 |
| 95% confidence interval | −16.3, −8.5 | −9.6, −1.8 | −17.7, −9.9 | −12.9, −8.4 |
| Week 3, n | 64 | 69 | 71 | 204 |
| Least squares mean ± SE | −11.5 ± 2.1 | −7.5 ± 2.0 | −12.5 ± 2.0 | −10.5 ± 1.2 |
| 95% confidence interval | −15.6, −7.4 | −11.5, −3.5 | −16.4, −8.6 | −12.8, −8.2 |
| Week 4, n | 65 | 67 | 69 | 201 |
| Least squares mean ± SE | −13.3 ± 2.0 | −8.0 ± 2.0 | −12.4 ± 2.0 | −11.2 ± 1.1 |
| 95% confidence interval | −17.2, −9.3 | −11.9, −4.1 | −16.2, −8.5 | −13.5, −9.0 |
| Week 5, n | 65 | 66 | 67 | 198 |
| Least squares mean ± SE | −12.0 ± 2.0 | −9.6 ± 2.0 | −13.7 ± 2.0 | −11.8 ± 1.2 |
| 95% confidence interval | −15.9, −8.0 | −13.5, −5.7 | −17.7, −9.8 | −14.0, −9.5 |
| Week 6, n | 65 | 66 | 64 | 195 |
| Least squares mean ± SE | −13.3 ± 2.1 | −6.9 ± 2.0 | −12.8 ± 2.1 | −11.0 ± 1.2 |
| 95% confidence interval | −17.3, −9.3 | −10.9, −2.9 | −16.8, −8.7 | −13.3, −8.7 |
| Week 7, n | 64 | 64 | 65 | 193 |
| Least squares mean ± SE | −15.6 ± 2.0 | −9.5 ± 2.0 | −11.0 ± 2.0 | −12.0 ± 1.2 |
| 95% confidence interval | −19.5, −11.6 | −13.6, −5.5 | −15.0, −7.0 | −14.3, −9.7 |
| Week 8, n | 66 | 64 | 66 | 196 |
| Least squares mean ± SE | −16.3 ± 2.0 | −12.0 ± 2.0 | −13.7 ± 2.0 | −14.0 ± 1.1 |
| 95% confidence interval | −20.2, −12.5 | −15.9, −8.1 | −17.7, −10.0 | −16.3, −11.8 |

TABLE 4

Estimated mean change from baseline in systolic blood pressure by randomized starting dose, all patients Stratum 2

| | Stratum 2—Local serum K+ >5.5-<6.0 mEq/L | | | |
|---|---|---|---|---|
| Change in SBP from baseline (mmHg) | 20 g/d N = 26 | 30 g/d N = 28 | 40 g/d N = 30 | Overall N = 84 |
| Patients in analysis, N | 26 | 28 | 29 | 83 |
| Day 3, n | 26 | 27 | 29 | 82 |
| Least squares mean ± SE | −7.3 ± 3.5 | −9.6 ± 3.4 | −6.6 ± 3.3 | −7.8 ± 2.0 |
| 95% confidence interval | −14.2, −0.4 | −16.3, −2.9 | −13.1, −0.08 | −11.7, −4.0 |
| Week 1, n | 24 | 28 | 28 | 80 |
| Least squares mean ± SE | −6.2 ± 4.2 | −11.5 ± 3.9 | −4.8 ± 3.9 | −7.5 ± 2.3 |
| 95% confidence interval | −14.4, 1.9 | −19.2, −3.9 | −12.5, 2.8 | −12.1, −3.0 |
| Week 2, n | 24 | 27 | 26 | 77 |
| Least squares mean ± SE | −5.8 ± 4.2 | −7.7 ± 4.0 | −3.3 ± 4.0 | −5.6 ± 2.4 |
| 95% confidence interval | −14.2, 2.5 | −15.6, 0.2 | −11.3, 4.6 | −10.3, −1.0 |
| Week 3, n | 24 | 25 | 25 | 74 |
| Least squares mean ± SE | −12.0 ± 3.8 | −10.0 ± 3.6 | −8.3 ± 3.6 | −10.1 ± 2.1 |
| 95% confidence interval | −19.4, −4.6 | −17.2, −2.9 | −15.5, −1.2 | −14.3, −5.9 |
| Week 4, n | 24 | 25 | 24 | 73 |
| Least squares mean ± SE | −9.6 ± 3.1 | −10.7 ± 3.0 | −3.8 ± 3.0 | −8.1 ± 1.7 |
| 95% confidence interval | −15.7, −3.5 | −16.6, −4.9 | −9.7, 2.1 | −11.5, −4.6 |
| Week 5, n | 24 | 25 | 23 | 72 |
| Least squares mean ± SE | −8.3 ± 3.6 | −9.4 ± 3.5 | −6.0 ± 3.5 | −7.9 ± 2.0 |
| 95% confidence interval | −15.3, −1.2 | −16.2, −2.7 | −13.0, 0.9 | −11.9, −3.9 |
| Week 6, n | 24 | 25 | 22 | 71 |
| Least squares mean ± SE | −7.5 ± 3.6 | −11.4 ± 3.4 | −5.4 ± 3.6 | −8.1 ± 2.0 |
| 95% confidence interval | −14.5, −0.5 | −18.1, −4.6 | −12.4, 1.6 | −12.1, −4.1 |
| Week 7, n | 24 | 25 | 22 | 71 |
| Least squares mean ± SE | −10.4 ± 3.4 | −8.4 ± 3.3 | −1.3 ± 3.4 | −6.7 ± 1.9 |
| 95% confidence interval | −17.1, −3.7 | −14.8, −1.9 | −8.0, 5.4 | −10.5, −2.9 |
| Week 8, n | 24 | 26 | 24 | 74 |
| Least squares mean ± SE | −7.8 ± 3.5 | −11.0 ± 3.4 | −1.7 ± 3.5 | −6.9 ± 2.0 |
| 95% confidence interval | −14.8, −0.9 | −17.6, −4.4 | −8.5, 5.1 | −10.8, −3.0 |

TABLE 5

Estimated mean change from baseline in systolic blood pressure by randomized starting dose, patients who were hyperkalemic at screening Stratum 1

| | Stratum 1—Local serum K+ >5.0-5.5 mEq/L | | | |
|---|---|---|---|---|
| Change in SBP from baseline (mmHg) | 10 g/d N = 57 | 20 g/d N = 57 | 30 g/d N = 56 | Overall N = 170 |
| Patients in analysis, N | 57 | 57 | 56 | 170 |
| Day 3, n | 56 | 56 | 56 | 168 |
| Least squares mean ± SE | −9.8 ± 2.0 | −5.6 ± 2.0 | −12.5 ± 2.0 | −9.3 ± 1.2 |
| 95% confidence interval | −13.8, −5.8 | −9.6, −1.6 | −16.5, −8.5 | −11.6, −7.0 |
| Week 1, n | 55 | 55 | 55 | 165 |
| Least squares mean ± SE | −11.4 ± 2.2 | −9.9 ± 2.2 | −12.7 ± 2.2 | −11.3 ± 1.3 |
| 95% confidence interval | −15.7, −7.1 | −14.2, −5.6 | −16.9, −8.4 | −13.8, −8.9 |
| Week 2, n | 54 | 54 | 54 | 162 |
| Least squares mean ± SE | −12.3 ± 2.3 | −5.8 ± 2.3 | −15.2 ± 2.3 | −11.1 ± 1.3 |
| 95% confidence interval | −16.8, −7.8 | −10.3, −1.3 | −19.8, −10.7 | −13.7, −8.5 |
| Week 3, n | 49 | 53 | 54 | 156 |
| Least squares mean ± SE | −11.6 ± 2.5 | −10.2 ± 2.4 | −13.8 ± 2.4 | −11.9 ± 1.4 |
| 95% confidence interval | −16.4, −6.7 | −14.9, −5.5 | −18.5, −9.1 | −14.6, −9.1 |
| Week 4, n | 51 | 52 | 53 | 156 |
| Least squares mean ± SE | −13.4 ± 2.3 | −10.8 ± 2.3 | −14.2 ± 2.3 | −12.8 ± 1.3 |
| 95% confidence interval | −18.0, −8.8 | −15.4, −6.3 | −18.7, −9.7 | −15.4, −10.2 |
| Week 5, n | 50 | 51 | 53 | 154 |
| Least squares mean ± SE | −11.4 ± 2.3 | −10.5 ± 2.3 | −15.0 ± 2.3 | −12.3 ± 1.3 |
| 95% confidence interval | −16.0, −6.8 | −15.1, −5.9 | −19.5, −10.5 | −14.9, −9.7 |
| Week 6, n | 50 | 51 | 52 | 153 |
| Least squares mean ± SE | −12.3 ± 2.2 | −6.8 ± 2.2 | −15.0 ± 2.2 | −11.4 ± 1.3 |
| 95% confidence interval | −16.6, −7.9 | −11.1, −2.5 | −19.3, −10.7 | −13.8, −8.9 |
| Week 7, n | 50 | 49 | 52 | 151 |
| Least squares mean ± SE | −14.5 ± 2.1 | −9.0 ± 2.1 | −13.2 ± 2.1 | −12.2 ± 1.2 |
| 95% confidence interval | −18.6, −10.3 | −13.2, −4.8 | −17.3, −9.1 | −14.6, −9.8 |
| Week 8, n | 51 | 49 | 52 | 152 |
| Least squares mean ± SE | −16.6 ± 2.2 | −13.0 ± 2.3 | −14.9 ± 2.2 | −14.8 ± 1.3 |
| 95% confidence interval | −21.0, −12.3 | −17.4, −8.6 | −19.2, −10.5 | −17.3, −12.3 |

TABLE 6

Estimated mean change from baseline in systolic blood pressure by randomized starting dose, patients who were hyperkalemic at screening Stratum 2

| Change in SBP from baseline (mmHg) | Stratum 2—Local serum K+ >5.5-<6.0 mEq/L | | | |
|---|---|---|---|---|
| | 20 g/d N = 24 | 30 g/d N = 24 | 40 g/d N = 25 | Overall N = 73 |
| Patients in analysis, N | 24 | 24 | 24 | 72 |
| Day 3, n | 24 | 23 | 24 | 71 |
| Least squares mean ± SE | −10.2 ± 3.6 | −11.2 ± 3.7 | −6.5 ± 3.7 | −9.3 ± 2.1 |
| 95% confidence interval | −17.3, −3.0 | −18.5, −3.9 | −13.6, 0.7 | −13.4, −5.1 |
| Week 1, n | 22 | 24 | 23 | 69 |
| Least squares mean ± SE | −8.4 ± 4.4 | −13.8 ± 4.3 | −2.1 ± 4.3 | −8.1 ± 2.5 |
| 95% confidence interval | −17.0, 0.3 | −22.2, −5.4 | −10.7, 6.4 | −13.0, −3.2 |
| Week 2, n | 22 | 23 | 21 | 66 |
| Least squares mean ± SE | −8.0 ± 4.3 | −10.4 ± 4.2 | −0.3 ± 4.3 | −6.2 ± 2.5 |
| 95% confidence interval | −16.4, 0.4 | −18.6, −2.1 | −8.8, 8.2 | −11.1, −1.4 |
| Week 3, n | 22 | 21 | 20 | 63 |
| Least squares mean ± SE | −14.1 ± 3.9 | −12.8 ± 3.9 | −6.7 ± 4.0 | −11.2 ± 2.3 |
| 95% confidence interval | −21.7, −6.4 | −20.5, −5.1 | −14.5, 1.2 | −15.6, −6.7 |
| Week 4, n | 22 | 21 | 19 | 62 |
| Least squares mean ± SE | −12.0 ± 3.2 | −13.6 ± 3.2 | −4.0 ± 3.3 | −9.9 ± 1.9 |
| 95% confidence interval | −18.3, −5.8 | −19.9, −7.3 | −10.6, 2.5 | −13.5, −6.2 |
| Week 5, n | 22 | 21 | 18 | 61 |
| Least squares mean ± SE | −10.1 ± 3.7 | −12.9 ± 3.8 | −4.1 ± 4.0 | −9.1 ± 2.2 |
| 95% confidence interval | −17.5, −2.8 | −20.3, −5.5 | −11.9, 3.7 | −13.4, −4.7 |
| Week 6, n | 22 | 21 | 17 | 60 |
| Least squares mean ± SE | −9.9 ± 3.5 | −14.2 ± 3.6 | −2.1 ± 3.8 | −8.7 ± 2.1 |
| 95% confidence interval | −16.8, −3.0 | −21.2, −7.2 | −9.6, 5.5 | −12.9, −4.6 |
| Week 7, n | 22 | 21 | 17 | 60 |
| Least squares mean ± SE | −12.7 ± 3.5 | −11.9 ± 3.5 | 1.9 ± 3.8 | −7.6 ± 2.1 |
| 95% confidence interval | −19.5, −5.9 | −18.8, −5.0 | −5.5, 9.4 | −11.6, −3.5 |
| Week 8, n | 22 | 22 | 19 | 63 |
| Least squares mean ± SE | −11.4 ± 3.6 | −14.4 ± 3.5 | −0.3 ± 3.8 | −8.7 ± 2.1 |
| 95% confidence interval | −18.4, −4.4 | −21.3, −7.4 | −7.7, 7.1 | −12.8, −4.6 |

Example 4: Analysis of Diastolic Blood Pressure from Phase II Clinical Study

This section contains results of the repeated measures analyses of diastolic blood pressure during the 8-week treatment initiation period of the Phase II Clinical Study disclosed in Example 2. Table 7 through Table 10 present the analyses of mean change in diastolic blood pressure from baseline. Tables 7 and 8 present the results for all patients; Tables 9 and 10 present subsets of the analyses according to hyperkalemia status at screening (Cohort 3). Patients in both cohorts and strata experienced modest mean reductions in diastolic blood pressure.

For Tables 7-10, column header counts include all randomized patients who received RLY5016 (intent-to-treat population) by each randomized starting dose within stratum. The data were derived from a mixed model for repeated measures where the outcome variable was a change in diastolic blood pressure (DBP) from baseline. Each stratum was analyzed separately. Each model contained a fixed effect for cohort, randomized starting dose, time (visit), continuous baseline DBP, and randomized starting dose by visit interaction. The within-patient correlation was modeled using heterogeneous Toeplitz structure. Estimates, standard errors (SE), and confidence intervals for each randomized starting dose were generated using linear contrasts across the observed values of the covariates. Overall estimates, standard errors, and confidence intervals across randomized dosing groups assume equal distribution across dosing groups. The total patients in the analysis, N, were determined by the number of randomized patients who received RLY5016, had a baseline measure, and contributed at least one post-baseline measure to this analysis. Not all patients contributed measures at each visit.

TABLE 7

Estimated mean change from baseline in diastolic blood pressure by randomized starting dose, all patients Stratum 1

| Change in DBP from baseline (mmHg) | Stratum 1—Local serum K+ >5.0-5.5 mEq/L | | | |
|---|---|---|---|---|
| | 10 g/d N = 74 | 20 g/d N = 73 | 30 g/d N = 73 | Overall N = 220 |
| Patients in analysis, N | 74 | 73 | 73 | 220 |
| Day 3, n | 70 | 70 | 72 | 212 |
| Least squares mean ± SE | −3.8 ± 1.1 | −3.1 ± 1.1 | −5.8 ± 1.1 | −4.2 ± 0.6 |
| 95% confidence interval | −6.0, −1.7 | −5.2, −1.0 | −7.9, −3.7 | −5.5, −3.0 |
| Week 1, n | 72 | 71 | 72 | 215 |
| Least squares mean ± SE | −6.0 ± 1.2 | −5.4 ± 1.2 | −7.0 ± 1.2 | −6.1 ± 0.7 |
| 95% confidence interval | −8.3, −3.7 | −7.7, −3.1 | −9.3, −4.7 | −7.4, −4.8 |

TABLE 7-continued

Estimated mean change from baseline in diastolic blood pressure by randomized starting dose, all patients Stratum 1

| Change in DBP from baseline (mmHg) | Stratum 1—Local serum K$^+$ >5.0-5.5 mEq/L | | | |
|---|---|---|---|---|
| | 10 g/d N = 74 | 20 g/d N = 73 | 30 g/d N = 73 | Overall N = 220 |
| Week 2, n | 70 | 70 | 71 | 211 |
| Least squares mean ± SE | −6.6 ± 1.3 | −6.1 ± 1.3 | −6.1 ± 1.3 | −6.3 ± 0.7 |
| 95% confidence interval | −9.0, −4.1 | −8.6, −3.6 | −8.6, −3.7 | −7.7, −4.8 |
| Week 3, n | 64 | 69 | 71 | 204 |
| Least squares mean ± SE | −5.0 ± 1.2 | −6.0 ± 1.2 | −8.0 ± 1.2 | −6.3 ± 0.7 |
| 95% confidence interval | −7.4, −2.5 | −8.4, −3.6 | −10.4, −5.7 | −7.7, −4.9 |
| Week 4, n | 65 | 67 | 69 | 201 |
| Least squares mean ± SE | −5.8 ± 1.2 | −6.5 ± 1.2 | −8.0 ± 1.2 | −6.7 ± 0.7 |
| 95% confidence interval | −8.1, −3.4 | −8.8, −4.1 | −10.3, −5.7 | −8.1, −5.4 |
| Week 5, n | 65 | 66 | 67 | 198 |
| Least squares mean ± SE | −6.0 ± 1.3 | −5.9 ± 1.3 | −8.4 ± 1.3 | −6.8 ± 0.7 |
| 95% confidence interval | −8.6, −3.5 | −8.5, −3.4 | −10.9, −5.9 | −8.2, −5.3 |
| Week 6, n | 65 | 66 | 64 | 195 |
| Least squares mean ± SE | −5.7 ± 1.3 | −6.4 ± 1.3 | −6.6 ± 1.3 | −6.2 ± 0.8 |
| 95% confidence interval | −8.3, −3.1 | −9.0, −3.8 | −9.2, −4.0 | −7.7, −4.8 |
| Week 7, n | 64 | 64 | 65 | 193 |
| Least squares mean ± SE | −6.3 ± 1.4 | −6.0 ± 1.4 | −6.5 ± 1.3 | −6.3 ± 0.8 |
| 95% confidence interval | −8.9, −3.6 | −8.7, −3.4 | −9.2, −3.9 | −7.8, −4.8 |
| Week 8, n | 66 | 64 | 66 | 196 |
| Least squares mean ± SE | −7.6 ± 1.4 | −7.3 ± 1.4 | −6.8 ± 1.4 | −7.2 ± 0.8 |
| 95% confidence interval | −10.3, −4.9 | −10.1, −4.6 | −9.5, −4.1 | −8.8, −5.7 |

TABLE 8

Estimated mean change from baseline in diastolic blood pressure by randomized starting dose, all patients Stratum 2

| Change in DBP from baseline (mmHg) | Stratum 2—Local serum K$^+$ >5.5-<6.0 mEq/L | | | |
|---|---|---|---|---|
| | 20 g/d N = 26 | 30 g/d N = 28 | 40 g/d N = 30 | Overall N = 84 |
| Patients in analysis, N | 26 | 28 | 29 | 83 |
| Day 3, n | 26 | 27 | 29 | 82 |
| Least squares mean ± SE | −1.7 ± 2.0 | −3.9 ± 2.0 | −5.4 ± 1.9 | −3.7 ± 1.1 |
| 95% confidence interval | −5.6, 2.3 | −7.8, −0.08 | −9.1, −1.7 | −5.9, −1.5 |
| Week 1, n | 24 | 28 | 28 | 80 |
| Least squares mean ± SE | −1.4 ± 2.5 | −5.3 ± 2.4 | −4.4 ± 2.3 | −3.7 ± 1.4 |
| 95% confidence interval | −6.4, 3.5 | −9.9, −0.7 | −9.0, 0.2 | −6.4, −1.0 |
| Week 2, n | 24 | 27 | 26 | 77 |
| Least squares mean ± SE | −7.2 ± 2.0 | −3.0 ± 1.9 | −5.5 ± 1.9 | −5.3 ± 1.1 |
| 95% confidence interval | −11.2, −3.3 | −6.8, 0.8 | −9.4, −1.7 | −7.5, −3.0 |
| Week 3, n | 24 | 25 | 25 | 74 |
| Least squares mean ± SE | −7.0 ± 2.1 | −7.1 ± 2.0 | −5.9 ± 2.0 | −6.7 ± 1.2 |
| 95% confidence interval | −11.1, −2.8 | −11.1, −3.1 | −9.9, −1.9 | −9.0, −4.3 |
| Week 4, n | 24 | 25 | 24 | 73 |
| Least squares mean ± SE | −7.7 ± 2.2 | −6.3 ± 2.2 | −1.9 ± 2.2 | −5.3 ± 1.3 |
| 95% confidence interval | −12.1, −3.3 | −10.6, −2.0 | −6.2, 2.4 | −7.8, −2.8 |
| Week 5, n | 24 | 25 | 23 | 72 |
| Least squares mean ± SE | −8.2 ± 1.8 | −6.8 ± 1.8 | −4.4 ± 1.8 | −6.5 ± 1.0 |
| 95% confidence interval | −11.8, −4.7 | −10.3, −3.4 | −8.0, −0.9 | −8.5, −4.5 |
| Week 6, n | 24 | 25 | 22 | 71 |
| Least squares mean ± SE | −7.1 ± 2.0 | −8.9 ± 2.0 | −4.3 ± 2.0 | −6.8 ± 1.2 |
| 95% confidence interval | −11.1, −3.1 | −12.8, −5.1 | −8.4, −0.3 | −9.1, −4.5 |
| Week 7, n | 24 | 25 | 22 | 71 |
| Least squares mean ± SE | −7.3 ± 1.9 | −9.0 ± 1.8 | −3.4 ± 1.9 | −6.6 ± 1.1 |
| 95% confidence interval | −10.9, −3.6 | −12.6, −5.4 | −7.1, 0.3 | −8.7, −4.5 |
| Week 8, n | 24 | 26 | 24 | 74 |
| Least squares mean ± SE | −4.5 ± 2.1 | −7.0 ± 2.0 | −1.8 ± 2.0 | −4.4 ± 1.2 |
| 95% confidence interval | −8.5, −0.4 | −10.9, −3.1 | −5.8, 2.2 | −6.7, −2.1 |

TABLE 9

Estimated mean change from baseline in diastolic blood pressure by randomized starting dose, patients who were hyperkalemic at screening Stratum 1

| | Stratum 1—Local serum $K^+$ >5.0-5.5 mEq/L | | | |
|---|---|---|---|---|
| Change in DBP from baseline (mmHg) | 10 g/d N = 57 | 20 g/d N = 57 | 30 g/d N = 56 | Overall N = 170 |
| Patients in analysis, N | 57 | 57 | 56 | 170 |
| Day 3, n | 56 | 56 | 56 | 168 |
| Least squares mean ± SE | −3.7 ± 1.3 | −4.5 ± 1.3 | −7.1 ± 1.3 | −5.1 ± 0.7 |
| 95% confidence interval | −6.1, −1.2 | −7.0, −2.0 | −9.6, −4.6 | −6.5, −3.7 |
| Week 1, n | 55 | 55 | 55 | 165 |
| Least squares mean ± SE | −5.8 ± 1.3 | −6.6 ± 1.3 | −7.5 ± 1.3 | −6.6 ± 0.8 |
| 95% confidence interval | −8.4, −3.2 | −9.2, −3.9 | −10.2, −4.9 | −8.1, −5.1 |
| Week 2, n | 54 | 54 | 54 | 162 |
| Least squares mean ± SE | −7.1 ± 1.5 | −7.4 ± 1.5 | −6.5 ± 1.5 | −7.0 ± 0.9 |
| 95% confidence interval | −10.0, −4.1 | −10.4, −4.5 | −9.5, −3.6 | −8.7, −5.3 |
| Week 3, n | 49 | 53 | 54 | 156 |
| Least squares mean ± SE | −5.2 ± 1.5 | −7.4 ± 1.4 | −9.7 ± 1.4 | −7.4 ± 0.8 |
| 95% confidence interval | −8.1, −2.2 | −10.2, −4.5 | −12.5, −6.8 | −9.0, −5.7 |
| Week 4, n | 51 | 52 | 53 | 156 |
| Least squares mean ± SE | −5.6 ± 1.4 | −8.5 ± 1.4 | −10.0 ± 1.3 | −8.0 ± 0.8 |
| 95% confidence interval | −8.2, −2.9 | −11.2, −5.9 | −12.6, −7.3 | −9.6, −6.5 |
| Week 5, n | 50 | 51 | 53 | 154 |
| Least squares mean ± SE | −6.5 ± 1.5 | −8.3 ± 1.5 | −9.5 ± 1.4 | −8.1 ± 0.8 |
| 95% confidence interval | −9.4, −3.6 | −11.1, −5.4 | −12.3, −6.7 | −9.7, −6.4 |
| Week 6, n | 50 | 51 | 52 | 153 |
| Least squares mean ± SE | −5.6 ± 1.5 | −7.3 ± 1.5 | −7.7 ± 1.5 | −6.8 ± 0.9 |
| 95% confidence interval | −8.6, −2.6 | −10.3, −4.3 | −10.7, −4.7 | −8.6, −5.1 |
| Week 7, n | 50 | 49 | 52 | 151 |
| Least squares mean ± SE | −5.5 ± 1.6 | −7.1 ± 1.6 | −7.7 ± 1.5 | −6.8 ± 0.9 |
| 95% confidence interval | −8.6, −2.4 | −10.2, −4.0 | −10.8, −4.7 | −8.5, −5.0 |
| Week 8, n | 51 | 49 | 52 | 152 |
| Least squares mean ± SE | −7.2 ± 1.6 | −8.1 ± 1.6 | −8.1 ± 1.6 | −7.8 ± 0.9 |
| 95% confidence interval | −10.4, −4.1 | −11.4, −4.9 | −11.3, −5.0 | −9.7, −6.0 |

TABLE 10

Estimated mean change from baseline in diastolic blood pressure by randomized starting dose, patients who were hyperkalemic at screening Stratum 2

| | Stratum 2—Local serum $K^+$ >5.5-<6.0 mEq/L | | | |
|---|---|---|---|---|
| Change in DBP from baseline (mmHg) | 20 g/d N = 24 | 30 g/d N = 24 | 40 g/d N = 25 | Overall N = 73 |
| Patients in analysis, N | 24 | 24 | 24 | 72 |
| Day 3, n | 24 | 23 | 24 | 71 |
| Least squares mean ± SE | −1.6 ± 2.2 | −4.1 ± 2.2 | −5.9 ± 2.2 | −3.9 ± 1.3 |
| 95% confidence interval | −5.9, 2.6 | −8.5, 0.3 | −10.1, −1.6 | −6.4, −1.4 |
| Week 1, n | 22 | 24 | 23 | 69 |
| Least squares mean ± SE | −1.5 ± 2.7 | −6.4 ± 2.7 | −4.4 ± 2.7 | −4.1 ± 1.6 |
| 95% confidence interval | −6.9, 3.9 | −11.6, −1.2 | −9.7, 0.9 | −7.2, −1.1 |
| Week 2, n | 22 | 23 | 21 | 66 |
| Least squares mean ± SE | −7.7 ± 2.2 | −4.0 ± 2.2 | −4.7 ± 2.2 | −5.5 ± 1.3 |
| 95% confidence interval | −12.0, −3.4 | −8.3, 0.2 | −9.0, −0.3 | −7.9, −3.0 |
| Week 3, n | 22 | 21 | 20 | 63 |
| Least squares mean ± SE | −7.2 ± 2.3 | −7.6 ± 2.3 | −6.9 ± 2.3 | −7.2 ± 1.3 |
| 95% confidence interval | −11.7, −2.7 | −12.1, −3.1 | −11.5, −2.3 | −9.9, −4.6 |
| Week 4, n | 22 | 21 | 19 | 62 |
| Least squares mean ± SE | −8.0 ± 2.4 | −6.9 ± 2.5 | −2.6 ± 2.6 | −5.8 ± 1.4 |
| 95% confidence interval | −12.7, −3.2 | −11.7, −2.0 | −7.6, 2.4 | −8.6, −3.0 |
| Week 5, n | 22 | 21 | 18 | 61 |
| Least squares mean ± SE | −8.6 ± 1.9 | −7.3 ± 2.0 | −5.1 ± 2.1 | −7.0 ± 1.1 |
| 95% confidence interval | −12.4, −4.9 | −11.2, −3.5 | −9.1, −1.0 | −9.3, −4.8 |
| Week 6, n | 22 | 21 | 17 | 60 |
| Least squares mean ± SE | −7.6 ± 2.1 | −10.0 ± 2.2 | −4.8 ± 2.3 | −7.5 ± 1.3 |
| 95% confidence interval | −11.8, −3.4 | −14.2, −5.8 | −9.3, −0.2 | −10.0, −5.0 |
| Week 7, n | 22 | 21 | 17 | 60 |
| Least squares mean ± SE | −7.5 ± 2.0 | −9.4 ± 2.1 | −3.0 ± 2.2 | −6.6 ± 1.2 |
| 95% confidence interval | −11.5, −3.5 | −13.5, −5.4 | −7.4, 1.4 | −9.0, −4.3 |
| Week 8, n | 22 | 22 | 19 | 63 |
| Least squares mean ± SE | −4.8 ± 2.2 | −8.6 ± 2.2 | −2.1 ± 2.3 | −5.2 ± 1.3 |
| 95% confidence interval | −9.1, −0.4 | −12.9, −4.3 | −6.7, 2.5 | −7.7, −2.6 |

Example 5: Study of Relationship Between Serum Potassium and Serum Aldosterone Levels Male, unilaterally nephrectomized, spontaneously hypertensive rats (SHR) (N=32) were used in the experimental groups in this study. Non-manipulated SHR (N=6) were used as a control group. Animals were acclimated on a low $Ca^{2+}$ and $Mg^{2+}$ diet (TD04498) for two weeks. The diet for the experimental groups was then switched to one supplemented with spironolactone (0.4% w/w, TD120436) and the drinking water was supplemented with amiloride (0.05 mM) and quinapril (30 mg/L) for the duration of the study.

Animals in the control group remained on the TD04498 diet and unsupplemented water for the duration of the study.

A baseline blood draw was performed on all animals 16 days later. The animals were randomized into 4 groups based on baseline serum potassium levels and placed on a potassium binder treatment regimen as described in the table below:

| Group | Treatment | N |
|---|---|---|
| 1 | TD120436 (untreated) | 8 |
| 2 | TD120436 + 2% potassium binder | 8 |
| 3 | TD120436 + 4% potassium binder | 8 |
| 4 | TD120436 + 6% potassium binder | 8 |
| 5 | Control | 6 |

Blood, feces, and urine were collected 9 and 15 days after the treatment regimen was started. Proximal and distal gastrointestinal segments were harvested at the end of the study. Serum, fecal, and urine potassium levels and serum aldosterone levels were determined at respective time points.

The serum potassium levels (mmol/L) for the control, untreated, and experimental groups at baseline, day 9, and day 15 were analyzed. The average serum potassium reduction levels compared to the untreated group were −9.1% (2% potassium binder), −18.2% (4% potassium binder), and −20.3% (6% potassium binder) on day 9 and −6.9% (2% potassium binder), −13.2% (4% potassium binder), and −17.4% (6% potassium binder) on day 15. A significant reduction in serum potassium levels in all groups treated with potassium binder at day 9 and at the two higher doses on day 15 was observed as compared to the untreated group. The analysis was performed using a 2-way ANOVA plus Bonferroni post hoc test (P<0.01; *P<0.001 vs. untreated).

The serum aldosterone levels (pg/mL) for the control, untreated, and experimental groups at baseline, day 9, and day 15 were also analyzed. The average serum aldosterone reduction levels compared to the untreated group were −22.7% (2% potassium binder), −53.0% (4% potassium binder), and −57.6% (6% potassium binder) on day 9 and −16.6% (2% potassium binder), −37.9% (4% potassium binder), and −50.3 (6% potassium binder) % on day 15. A significant reduction in serum aldosterone levels was observed in all groups treated with potassium binder at day 9 and at the two higher doses on day 15 as compared to the untreated group. The analysis was performed using a 2-way ANOVA plus Bonferroni post-hoc test (*P<0.05; P<0.01; *P<0.001 vs. untreated).

There was no difference in the urine potassium excretion levels between all treatment groups.

The study showed that a reduction in serum aldosterone was observed with a reduction in serum potassium.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying figure[s] shall be interpreted as illustrative and not in a limiting sense.

What is claimed is:

1. A method of treating hyperkalemia in a human patient in need thereof optionally being treated with an effective amount of a renin-angiotensin-aldosterone system (RAAS) agent, the method comprising:
    administering to the human patient sorbitol-loaded, crosslinked (calcium 2-fluoroacrylate)-divinylbenzene-1,7-octadiene copolymer at a once daily dose of between 10 g and 40 g wherein the dose is calculated by determining the amount of calcium 2-fluoroacrylate-divinylbenzene-1,7-octadiene copolymer anion plus the amount of calcium counterion;
    wherein the human patient was hyperkalemic before treatment with the sorbitol-loaded, crosslinked (calcium 2-fluoroacrylate)-divinylbenzene-1,7-octadiene copolymer;
    wherein the human patient was normokalemic after 4 weeks of treatment with the sorbitol-loaded, crosslinked (calcium 2-fluoroacrylate)-divinylbenzene-1,7-octadiene copolymer; and
    wherein the sorbitol-loaded, crosslinked (calcium 2-fluoroacrylate)-divinylbenzene-1,7-octadiene copolymer is prepared by slurrying cross-linked (calcium 2-fluoroacrylate)-divinylbenzene-1,7-octadiene copolymer with a sorbitol solution.

2. The method of claim 1, further comprising observing an increase or stabilization of estimated glomerular filtration rate (eGFR) as compared to the patient's eGFR before treatment with the sorbitol-loaded, crosslinked (calcium 2-fluoroacrylate)-divinylbenzene-1,7-octadiene copolymer.

3. The method of claim 1, further comprising observing a decrease in the patient's serum creatinine level as compared to the patient's serum creatinine level before treatment with the sorbitol-loaded, crosslinked (calcium 2-fluoroacrylate)-divinylbenzene-1,7-octadiene copolymer.

4. The method of claim 1, further comprising observing an increase in the time to progression of end stage renal disease as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

5. The method of claim 1, further comprising observing an increase in survival as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

6. The method of claim 2, wherein the increase or stabilization of eGFR is maintained over more than 12 weeks during which the sorbitol-loaded, crosslinked (calcium 2-fluoroacrylate)-divinylbenzene-1,7-octadiene copolymer is administered to the patient daily.

7. The method of claim 2, wherein the increase or stabilization of eGFR is maintained over more than 24 weeks during which the sorbitol-loaded, crosslinked (calcium 2-fluoroacrylate)-divinylbenzene-1,7-octadiene copolymer is administered to the patient daily.

8. The method of claim 2, wherein the increase or stabilization of eGFR is maintained over 52 weeks or more during which the sorbitol-loaded, crosslinked (calcium 2-fluoroacrylate)-divinylbenzene-1,7-octadiene copolymer is administered to the patient daily.

9. The method of claim 8, wherein the patient's eGFR after treatment with the sorbitol-loaded, crosslinked (calcium 2-fluoroacrylate)-divinylbenzene-1,7-octadiene copolymer increased by at least 4 mL/min/1.73 m$^2$ or more as compared to the patient's eGFR before treatment with the sorbitol-loaded, crosslinked (calcium 2-fluoroacrylate)-divinylbenzene-1,7-octadiene copolymer.

10. The method of claim 1, wherein the patient's serum potassium level is decreased after 2 days or more of treatment as compared to the patient's serum potassium level before treatment with the sorbitol-loaded, crosslinked (calcium 2-fluoroacrylate)-divinylbenzene-1,7-octadiene copolymer, and the decreased serum potassium level is maintained over the 52 weeks or more of treatment.

11. The method of claim 2, further comprising observing a decrease in the patient's serum creatinine level as compared to the patient's serum creatinine level before treatment with the sorbitol-loaded, crosslinked (calcium 2-fluoroacrylate)-divinylbenzene-1,7-octadiene copolymer.

12. The method of claim 2, further comprising observing an increase in the time to progression of end stage renal disease as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

13. The method of claim 11, further comprising observing an increase in the time to progression of end stage renal disease as compared a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

14. The method of claim 2, further comprising observing an increase in survival as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

15. The method of claim 11, further comprising observing an increase in survival as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

16. The method of claim 12, further comprising observing an increase in survival as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

17. The method of claim 13, further comprising observing an increase in survival as compared to a patient in need of treatment for hyperkalemia wherein the patient has chronic kidney disease optionally treated with a RAAS agent but not treated with the sorbitol-loaded, crosslinked (calcium 2-fluoroacrylate)-divinylbenzene-1,7-octadiene copolymer.

18. The method of claim 1, wherein the patient's albumin:creatinine ratio is stabilized after 3 months or more of treatment.

19. The method of claim 1, wherein the patient is being treated with a RAAS agent.

20. The method of claim 1, wherein the patient had a serum potassium level of greater than 5.0 mEq/L before treatment with the sorbitol-loaded, crosslinked (calcium 2-fluoroacrylate)-divinylbenzene-1,7-octadiene copolymer.

21. The method of claim 1, wherein the patient had a serum potassium level of greater than or equal to 5.1 mEq/L before treatment with the sorbitol-loaded, crosslinked (calcium 2-fluoroacrylate)-divinylbenzene-1,7-octadiene copolymer.

22. The method of claim 1, wherein the patient had a serum potassium level of greater than or equal to 5.5 mEq/L before treatment with the sorbitol-loaded, crosslinked (calcium 2-fluoroacrylate)-divinylbenzene-1,7-octadiene copolymer.

23. The method of claim 20, wherein the patient had a serum potassium level of less than or equal to 5.0 mEq/L after 4 weeks of treatment with the sorbitol-loaded, crosslinked (calcium 2-fluoroacrylate)-divinylbenzene-1,7-octadiene copolymer.

24. The method of claim 1, wherein the patient had a serum potassium level of less than or equal to 5.0 mEq/L after 4 weeks of treatment with the sorbitol-loaded, crosslinked (calcium 2-fluoroacrylate)-divinylbenzene-1,7-octadiene copolymer.

25. A method of treating hyperkalemia in a human patient in need thereof optionally being treated with an effective amount of a renin-angiotensin-aldosterone system (RAAS) agent, the method comprising:
    administering to the human patient sorbitol-loaded, crosslinked (calcium 2-fluoroacrylate)-divinylbenzene-1,7-octadiene copolymer;
    wherein the starting dose of sorbitol-loaded, crosslinked (calcium 2-fluoroacrylate)-divinylbenzene-1,7-octadiene copolymer is 8.4 grams anion daily;
    wherein the human patient was hyperkalemic before treatment with the sorbitol-loaded, crosslinked (calcium 2-fluoroacrylate)-divinylbenzene-1,7-octadiene copolymer; and
    wherein the sorbitol-loaded, crosslinked (calcium 2-fluoroacrylate)-divinylbenzene-1,7-octadiene copolymer is prepared by slurrying cross-linked (calcium 2-fluoroacrylate)-divinylbenzene-1,7-octadiene copolymer with a sorbitol solution.

26. The method of claim 25, wherein the patient was normokalemic after 4 weeks of treatment with the sorbitol-loaded, crosslinked (calcium 2-fluoroacrylate)-divinylbenzene-1,7-octadiene copolymer.

27. The method of claim 25, wherein the patient had a serum potassium level of greater than 5.0 mEq/L before treatment with the sorbitol-loaded, crosslinked (calcium 2-fluoroacrylate)-divinylbenzene-1,7-octadiene copolymer.

28. The method of claim 25, wherein the patient had a serum potassium level of greater than or equal to 5.1 mEq/L before treatment with the sorbitol-loaded, crosslinked (calcium 2-fluoroacrylate)-divinylbenzene-1,7-octadiene copolymer.

29. The method of claim 25, wherein the patient had a serum potassium level of greater than or equal to 5.5 mEq/L before treatment with the sorbitol-loaded, crosslinked (calcium 2-fluoroacrylate)-divinylbenzene-1,7-octadiene copolymer.

30. The method of claim 25, wherein the patient had a serum potassium level of less than or equal to 5.0 mEq/L after 4 weeks of treatment with the sorbitol-loaded, crosslinked (calcium 2-fluoroacrylate)-divinylbenzene-1,7-octadiene copolymer.

31. The method of claim 29, wherein the patient had a serum potassium level of less than or equal to 5.0 mEq/L after 4 weeks of treatment with the sorbitol-loaded, crosslinked (calcium 2-fluoroacrylate)-divinylbenzene-1,7-octadiene copolymer.

32. The method of claim 1, wherein cross-linked (calcium 2-fluoroacrylate)-divinylbenzene-1,7-octadiene copolymer was slurried with 25 wt.% to 30% wt.% aqueous sorbitol solution at ambient temperature.

33. The method of claim 25, wherein cross-linked (calcium 2-fluoroacrylate)-divinylbenzene-1,7-octadiene copolymer was slurried with 25 wt.% to 30% wt.% aqueous sorbitol solution at ambient temperature.

\* \* \* \* \*

UNITED STATES PATENT AND TRADEMARK OFFICE
CERTIFICATE OF CORRECTION

PATENT NO. : 11,123,363 B2
APPLICATION NO. : 15/916617
DATED : September 21, 2021
INVENTOR(S) : Gerrit Klaerner et al.

It is certified that error appears in the above-identified patent and that said Letters Patent is hereby corrected as shown below:

In the Claims

On Column 52, Claim 1, Line 26:
"the amount of calcium 2-fluoroacrylate-"
Should read:
"the amount of 2-fluoroacrylate-"

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*